(12) United States Patent
Tang et al.

(10) Patent No.: US 11,332,449 B2
(45) Date of Patent: May 17, 2022

(54) AIE-ACTIVE CHEMO SENSORS FOR AMINE DETECTION AND RELATED FOOD-SAFETY MONITORING

(71) Applicant: THE HONG KONG UNIVERSITY OF SCIENCE AND TECHNOLOGY, Hong Kong (CN)

(72) Inventors: Benzhong Tang, Hong Kong (CN); Parvej Alam, Hong Kong (CN); Nelson Lik Ching Leung, Hong Kong (CN)

(73) Assignee: THE HONG KONG UNIVERSITY OF SCIENCE AND TECHNOLOGY, Hong Kong (CN)

(*) Notice: Subject to any disclaimer, the term of this patent is extended or adjusted under 35 U.S.C. 154(b) by 166 days.

(21) Appl. No.: 16/613,370

(22) PCT Filed: May 16, 2018

(86) PCT No.: PCT/CN2018/087126
§ 371 (c)(1),
(2) Date: Nov. 13, 2019

(87) PCT Pub. No.: WO2018/210272
PCT Pub. Date: Nov. 22, 2018

(65) Prior Publication Data
US 2020/0062718 A1 Feb. 27, 2020

Related U.S. Application Data

(60) Provisional application No. 62/603,058, filed on May 17, 2017.

(51) Int. Cl.
G01N 33/12 (2006.01)
G01N 21/78 (2006.01)
(Continued)

(52) U.S. Cl.
CPC ............ *C07D 241/42* (2013.01); *G01N 21/77* (2013.01); *G01N 21/78* (2013.01); *G01N 33/12* (2013.01);
(Continued)

(58) Field of Classification Search
CPC .................. G01N 21/77; G01N 21/78; G01N 2021/7759; G01N 31/22; G01N 33/02;
(Continued)

(56) References Cited

U.S. PATENT DOCUMENTS

2006/0240565 A1 10/2006 Tang et al.
2013/0059392 A1 3/2013 Tang et al.

FOREIGN PATENT DOCUMENTS

CN 106632088 A 5/2017

OTHER PUBLICATIONS

Xie, C. et al. "An efficient iodine-DMSO catalyzed synthesis of quinoxaline derivatives," Tetrahedron 71 (2015) 1831-1837 (Year: 2015).*

(Continued)

Primary Examiner — Jennifer Wecker
Assistant Examiner — Michelle Adams
(74) Attorney, Agent, or Firm — Nath, Goldberg & Meyer; Joshua B. Goldberg

(57) ABSTRACT

AIE-active chemosensors, according to the present teachings, exhibit UV-vis absorption change and become non-luminescent upon protonation. Upon deprotonation, the chemosensors revert to their original absorption and emission. This deprotonation process can be triggered in the presence of amines, and specifically, biogenic amines. The chemosensors can detect amine species, e.g., biogenic amines produced during food fermentation, quickly and with high sensitivity. Further, due to the AIE nature of the compounds, (Continued)

the chemosensors can be loaded onto a physical support and sealed inside a food package to monitor food spoilage.

15 Claims, 26 Drawing Sheets

(51) Int. Cl.
    *C07D 241/42*     (2006.01)
    *G01N 21/77*     (2006.01)

(52) U.S. Cl.
    CPC .............. *G01N 2021/7759* (2013.01); *Y10T 436/173845* (2015.01); *Y10T 436/175383* (2015.01)

(58) Field of Classification Search
    CPC .......... G01N 33/12; Y10T 436/173845; Y10T 436/175383; C07D 241/40; C07D 241/42; C07D 241/44
    See application file for complete search history.

(56) References Cited

OTHER PUBLICATIONS

Son, H.-J. et al. "Fluorescence Control on Panchromatic Spectra via C-Alkylation on Arylated Quinoxalines," J. Org. Chem. 2009, 74, 3175-3178 (Year: 2009).*

Kolos, N.N. et al. "3-Aryl-1,2-dihydroquinoxalines," Chem Heterocycl Compd 22, 918-922 (1986). Translated from Khimiya Geterotsiklicheskikh Soedinenii, No. 8, pp. 1127-1132, Aug. 1986. (Year: 1986).*

International Search Report for PCT/CN2018/087126 dated Aug. 22, 2018.

Gao, Meng et al. "Fluorescent light-up detection of amine vapors based on aggregation-induced emission", ACS Sensors Dec. 8, 2015, No. 2, vol. 1, pp. 179-184.

Son, Ho-Jin et al., "Turning on Fluorescent Emission from C-Alkylation on Quinoxaline Derivatives", Organic Letters, Oct. 31, 2008, No. 23, vol. 10, pp. 5401-5404.

Mazumdar, Prativa et al., "Proton triggered emission and selective sensing of picric acid by the fluorescent aggregates of 6,7-dimethyl-2,3-bis-(2-pyridyl)-quinoxaline", Phys. Chem. Chem. Phys. Mar. 14, 2016, No. 10 , vol. 18, pp. 7055-7067.

Chopra, Shweta et al., "Organic Nonoparticles for Visual Detection of Spermidine and Spermine in Vapors and Aqueous Phase", ACS Sustainable Chemistry & Engineering, Dec. 20, 2016, vol. 5, pp. 1287-1296.

Alam, Parvej et al., "A highly Sensitive Bimodal Detection of Amine Vapours Based on Aggregation Induced Emission f 1,2-Dihydroquinoxaline Derivatives", Chem. Eur J., Aug. 10, 2017, No. 59, vol. 23, pp. 14911-14917.

* cited by examiner

AIE-ACTIVE CHEMO SENSORS FOR AMINE DETECTION AND RELATED FOOD-SAFETY MONITORING

CROSS-REFERENCE

The present application claims priority to provisional U.S. Patent Application No. 62/603,058, filed May 17, 2017, which was filed by the inventors hereof and is incorporated herein by reference in its entirety.

FIELD

The present subject matter relates generally to a series of compounds with aggregation-induced emission (AIE) characteristics and their applications as chemosensors to monitor food spoilage by detecting amine species.

BACKGROUND

Human health and food safety must be considered when packaging and shipping raw food. Refrigeration processes have greatly increased the distances that raw food can travel by maintaining low temperatures to hinder the growth of microbes that lead to food spoilage. Many methods have been designed to monitor the shipping process, such as time-temperature indicators (TTI) to show whether raw food materials have been stored at elevated temperatures for an extended duration of time. However, maintaining a chilled temperature only slows down the enzymatic processes of food spoilage. Indeed, biogenic amine species, such as putrescine and cadaverine, produced by microbes have been found in rainbow trout stored at 0° C. by the second day.

Biogenic amines are good indicators of food freshness because they are products of microbial fermentation. In the process of food spoilage, microbes break down amino acids via deaminization to generate ammonia, and via decarboxylation to generate biogenic amines such as cadaverine, putrescine, spermidine, spermine, and others. These biogenic amines not only signal food spoilage, but also have adverse impact on human health and physiological functions. Thus, monitoring biogenic amines in food is important both because the chemical species can have toxic effects, and because they signify food spoilage by microbes. When compared to TTIs, which only respond to temperature changes, a system detecting the presence of biogenic amines offers a more direct method of monitoring food safety and hygiene.

The detection of biogenic amines can be achieved by exploiting their basic nature using a chemical sensor that shows photophysical changes upon protonation/deprotonation. In fact, there are many molecular species which have visible color change (i.e., absorption change) upon protonation/deprotonation. Such a visual change allows for easy visualization of changes due to the presence of biogenic amines.

An ideal system for detection of biogenic amines would show not only absorption but also luminescence change. Luminescent systems can be much more sensitive to changes, resulting in significantly easier identification. Previous work in this area focused on systems showing absorption and luminescence changes to amine species in solution. Solution-based systems are difficult to put into use due to inherent logistical issues. Conventional luminescent systems also often experience a reduction in emission intensity due to the aggregation-caused quenching (ACQ) effect.

Therefore, AIE-active chemosensors for amine detection and food safety monitoring are desired.

SUMMARY

AIE-active chemosensors, according to the present teachings, exhibit UV-vis absorption change and become non-luminescent upon protonation. Upon deprotonation, the chemosensors revert to their original absorption and emission patterns. This deprotonation process can be triggered in the presence of amines, and specifically, biogenic amines. The chemosensors can detect amine species, e.g., biogenic amines produced during food fermentation, quickly and with high sensitivity. Further, due to the AIE nature of the compounds, the chemosensors can be loaded onto a physical support and sealed inside a food package to monitor food spoilage.

In an embodiment, the present AIE chemosensor comprises a compound that exhibits aggregation induced emission properties, wherein the compound comprises a backbone structure selected from the group consisting of:

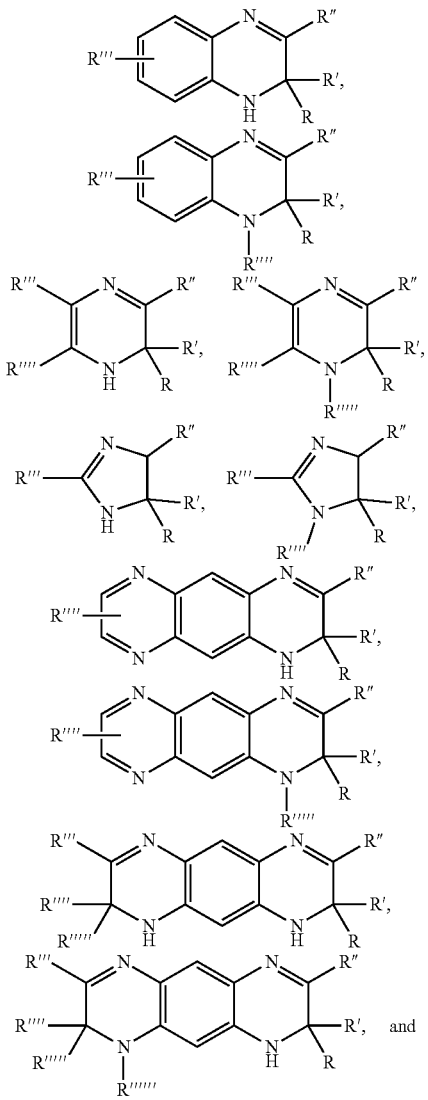

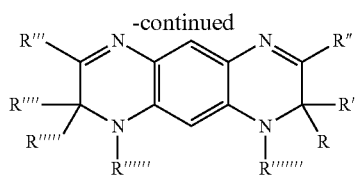

wherein R, R', R", R'", R"", R""', R"""', and R"""" are each independently selected from the group consisting of $C_nH_{2n+1}$, $C_6H_5$, $C_{10}H_7$, $C_{12}H_9$, $OC_6H_5$, $OC_{10}H_7$, $OC_{12}H_9$, $C_nH_{2n}COOH$, $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

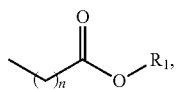

wherein $R_1$ is selected from the group consisting of $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

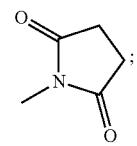

wherein n is between 0 and 20;

wherein at least one of R, R', R", R'", R"", R""', R""", and R"""" is other than H; and wherein when any of R, R', R", R'", R"", R""', R""", and R"""" is $C_6H_5$, it can be further substituted with an alkyl group or a phenyl.

In an embodiment, the present AIE chemosensor comprises a compound that exhibits aggregation induced emission properties, wherein the compound comprises a backbone structure of:

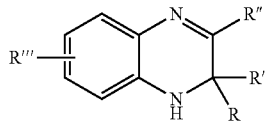

wherein R, R', R", and R'" are each independently selected from the group consisting of $C_nH_{2n+1}$, $C_6H_5$, $C_{10}H_7$, $C_{12}H_9$, $OC_6H_5$, $OC_{10}H_7$, $OC_{12}H_9$, $C_nH_{2n}COOH$, $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

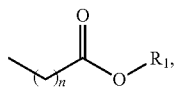

wherein $R_1$ is selected from the group consisting of $C_nH_{2n}NCS$, $C_nH_{2n}N_3$, $C_nH_{2n}NH_2$, $C_nH_{2n}Cl$, $C_nH_{2n}Br$, $C_nH_{2n}I$, and wherein n is between 0 and 20;

wherein at least one of R, R', R", and R'" is other than H; and wherein when any of R, R', R", and R'" is $C_6H_5$, it can be further substituted with an alkyl group or a phenyl.

In a further embodiment, the AIE chemosensor comprises a compound that exhibits aggregation induced emissions properties, wherein the compound comprises a backbone structure selected from the group consisting of:

(DQ1)

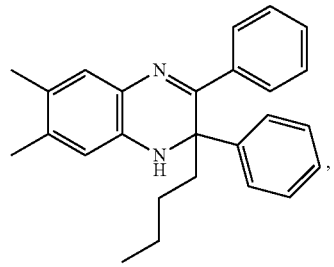

(DQ2)

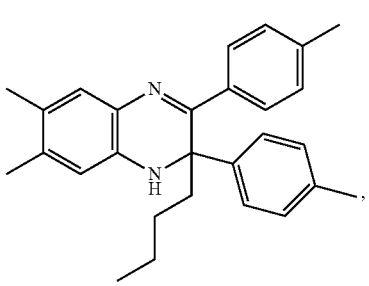

(DQ3)

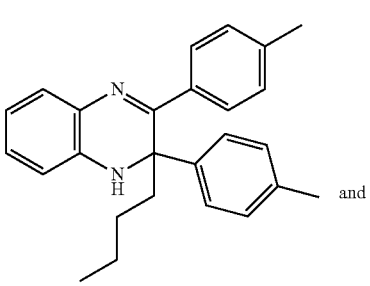

and (DQ4)

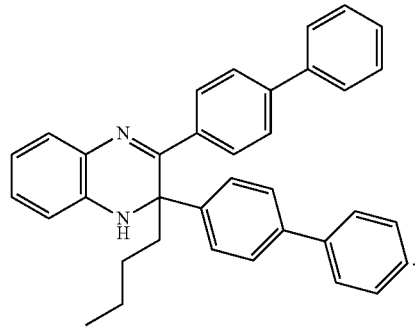

BRIEF DESCRIPTION OF DRAWINGS

Various embodiments will now be described in detail with reference to the accompanying drawings.

DETAILED DESCRIPTION

Figure 1A:
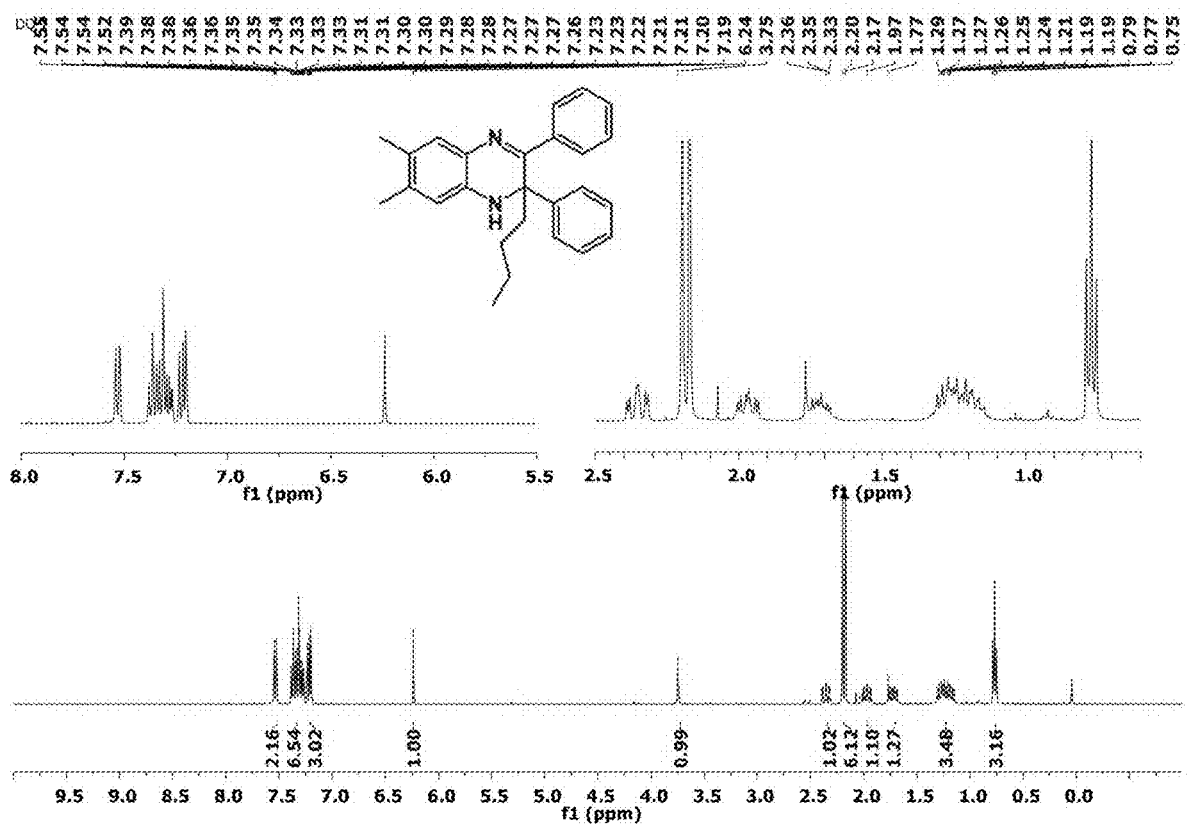
FIG. 1A depicts a $^1$H NMR spectrum of DQ1 in CDCl$_3$.
Figure 1B:
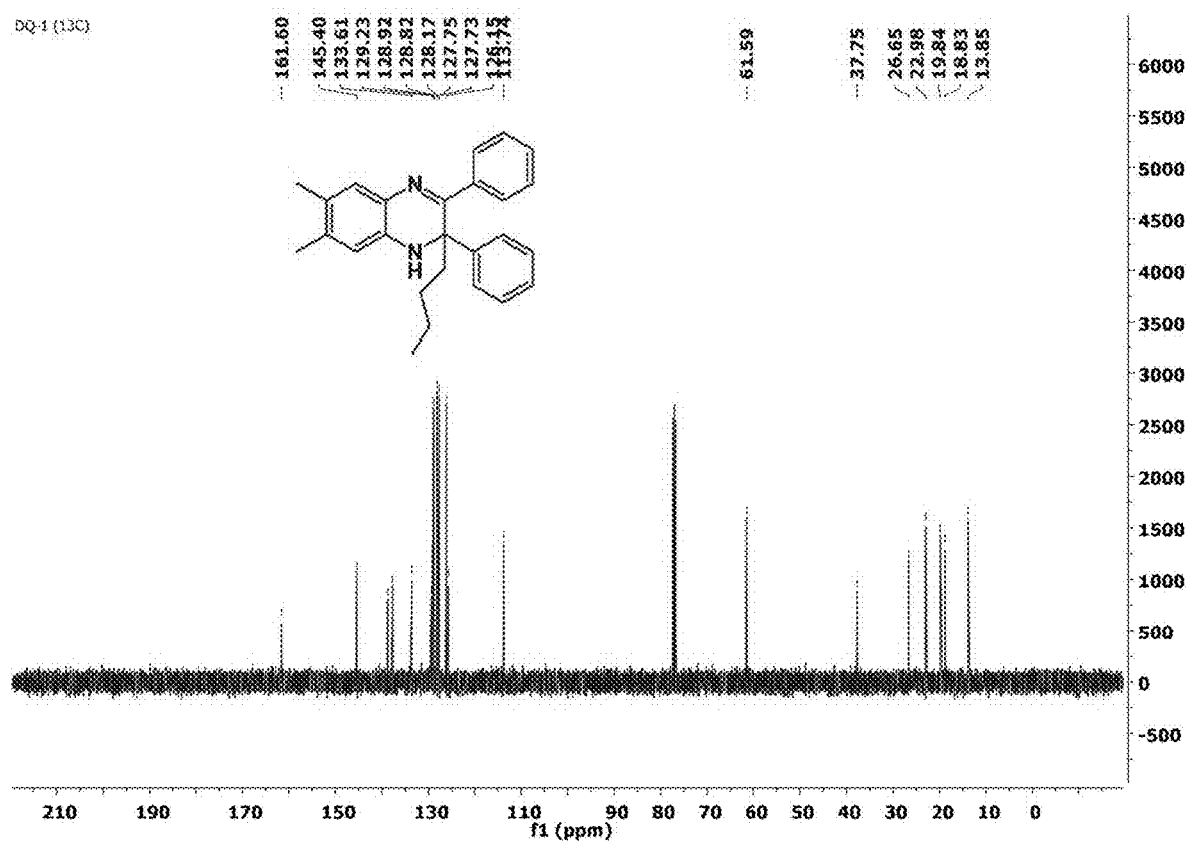
FIG. 1B depicts a $^{13}$C NMR spectrum of DQ1 in CDCl$_3$.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., -C6F5), are included within the definition of "haloaryl." In certain embodiments, an aryl group is substituted with another aryl group and can be referred to as a biaryl group. Each of the aryl groups in the biaryl group can be substituted as disclosed herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

AIE Chemosensors

In an embodiment, the present AIE chemosensor comprises a compound that exhibits aggregation induced emission properties, wherein the compound comprises a backbone structure selected from the group consisting of:

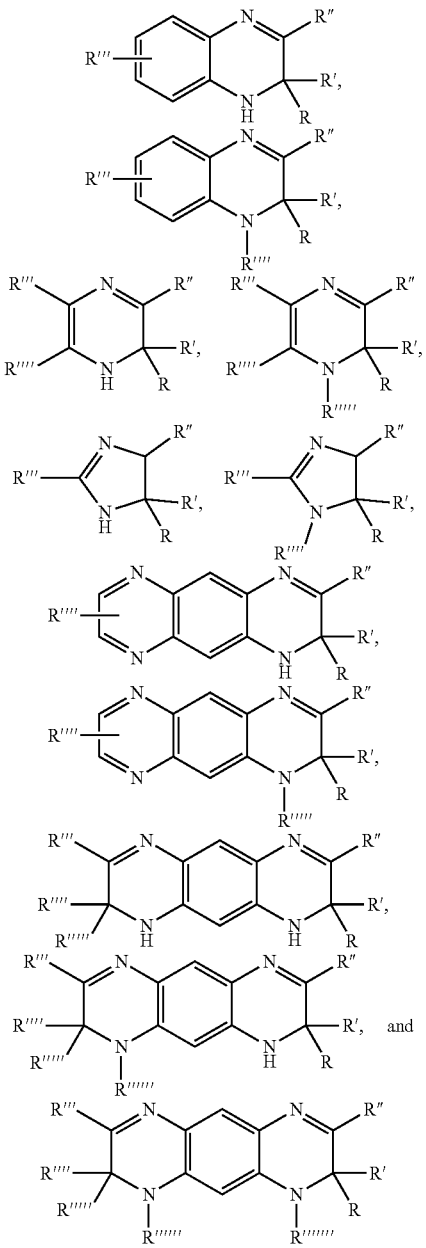

wherein R, R', R", R''', R'''', R''''', R'''''', and R''''''' are each independently selected from the group consisting of $C_nH_{2n+1}$, $C_6H_5$, $C_{10}H_7$, $C_{12}H_9$, $OC_6H_5$, $OC_{10}H_7$, $OC_{12}H_9$, $C_nH_{2n}COOH$, $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

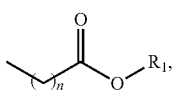

wherein $R_1$ is selected from the group consisting of $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

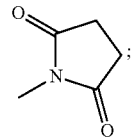

wherein n is between 0 and 20;

wherein at least one of R, R', R", R''', R'''', R''''', R'''''', and R''''''' is other than H; and wherein when any of R, R', R", R''', R'''', R''''', R'''''', and R''''''' is $C_6H_5$, it can be further substituted with an alkyl group or a phenyl.

In an embodiment, the present AIE chemosensor comprises a compound that exhibits aggregation induced emission properties, wherein the compound comprises a backbone structure of:

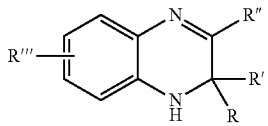

wherein R, R', R", and R''' are each independently selected from the group consisting of $C_nH_{2n+1}$, $C_6H_5$, $C_{10}H_7$, $C_{12}H_9$, $OC_6H_5$, $OC_{10}H_7$, $OC_{12}H_9$, $C_nH_{2n}COOH$, $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

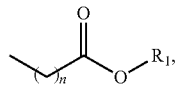

wherein $R_1$ is selected from the group consisting of $C_nH_{2n}NCS$, $C_nH_{2n}N_3$, $C_nH_{2n}NH_2$, $C_nH_{2n}Cl$, $C_nH_{2n}Br$, $C_nH_{2n}I$, and

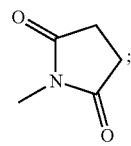

wherein n is between 0 and 20; and wherein at least one of R, R', R", and R''' is other than H; and wherein when any of R, R', R", and R''' is $C_6H_5$, it can be further substituted with an alkyl group or a phenyl.

In a further embodiment, the AIE chemosensor comprises a compound that exhibits aggregation induced emission properties, wherein the compound comprises a backbone structure selected from the group consisting of:

(DQ1)

(DQ2)

(DQ3)

and (DQ4)

In an embodiment, the AIE chemosensor comprises a compound that exhibits aggregation induced emission properties, wherein the compound comprises a backbone structure of:

(DQ2)

An exemplary reaction scheme for preparing an AIE chemosensor (specifically, a dihydroquinoxaline derivative) is provided below:

$R_1 = $ Me, H
$R_2 = $ Me, Ph
$R_3 = $ Bu

The present compounds can include protonated dihydroquinoxaline derivatives. The protonated dihydroquinoxaline derivatives can exhibit UV-vis absorption change and can be non-emissive. In an embodiment, when protonated, the dihydroquinoxaline derivatives herein are protonated at the unsubstituted imine nitrogen.

Once protonated, upon deprotonation, the chemosensors can revert to their original absorption and emission. This deprotonation process can be triggered by exposure to amines, and specifically, biogenic amines. Further, the deprotonation of the imine nitrogen can produce a detectable change in light absorption and/or a detectable change in light emission.

Detecting Food Spoilage

Accordingly, the chemosensors can be useful for detecting solution or gaseous samples of amines, e.g., biogenic amines produced during food fermentation. In this regard, the chemosensors can exhibit aggregation induced emission (AIE) upon exposure to an amine, for example, the biogenic amines produced during food fermentation. The amines that can be detected, and that can cause AIE, include gaseous amines. The chemosensors can detect the biogenic amines quickly and with high sensitivity. The chemosensors can achieve detection in an aggregated and/or solid state. Further, due to the AIE nature of the compounds, the chemosensors can be loaded onto a physical support and sealed inside a food package to monitor food spoilage.

In this regard, an embodiment herein is directed to a method of detecting food spoilage in a sample, comprising administering an AIE chemosensor herein to the sample; and detecting the presence of food spoilage in the sample by measuring light emission. In an embodiment, the method further comprises waiting for a period of time after administering the AIE chemosensor and before detecting the present of food spoilage. In some embodiments, the period of time can be short, e.g., about 1 minute, 2 minutes, 3 minutes, 4, minutes, or 5 minutes, as the AIE chemosensor can detect food spoilage quickly. In an embodiment, the period of time can be about 5 minutes. In other embodiments, the period of time can be overnight, for example, 12 hours or more. In these embodiments, the additional waiting time provides further opportunity for the food decomposition to occur. That being said, once the waiting step has passed, the detection of the specific biogenic amines occurs quickly.

In this regard, the AIE chemosensor can be loaded onto a physical support, by way of non-limiting example, a filter paper strip, prior to administering the AIE chemosensor to the sample. In an embodiment, the sample is a packaged food product. Other, non-limiting, exemplary physical supports on which the AIE chemosensor can be loaded include a glass microfiber filter and a glass slide.

Figure 9:
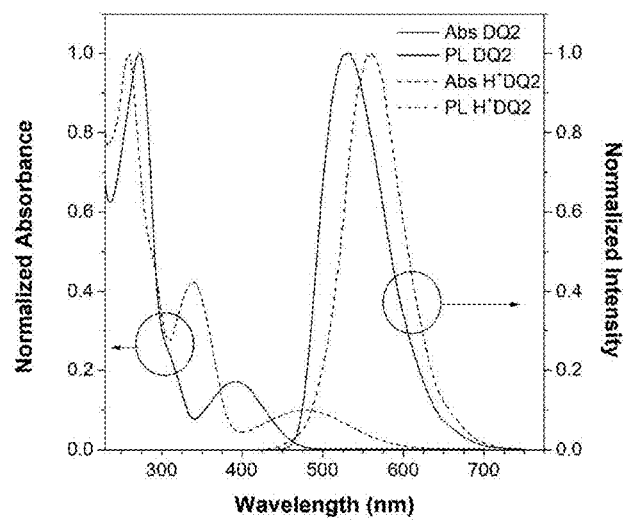
FIG. 9 depicts the UV and photoluminescence (PL) spectra of DQ2 and H$^+$DQ2 in DCM (Concentration of DQ2 ($C_{DQ2}$)=10 µM).
Figures 10A, 10B, 10C:
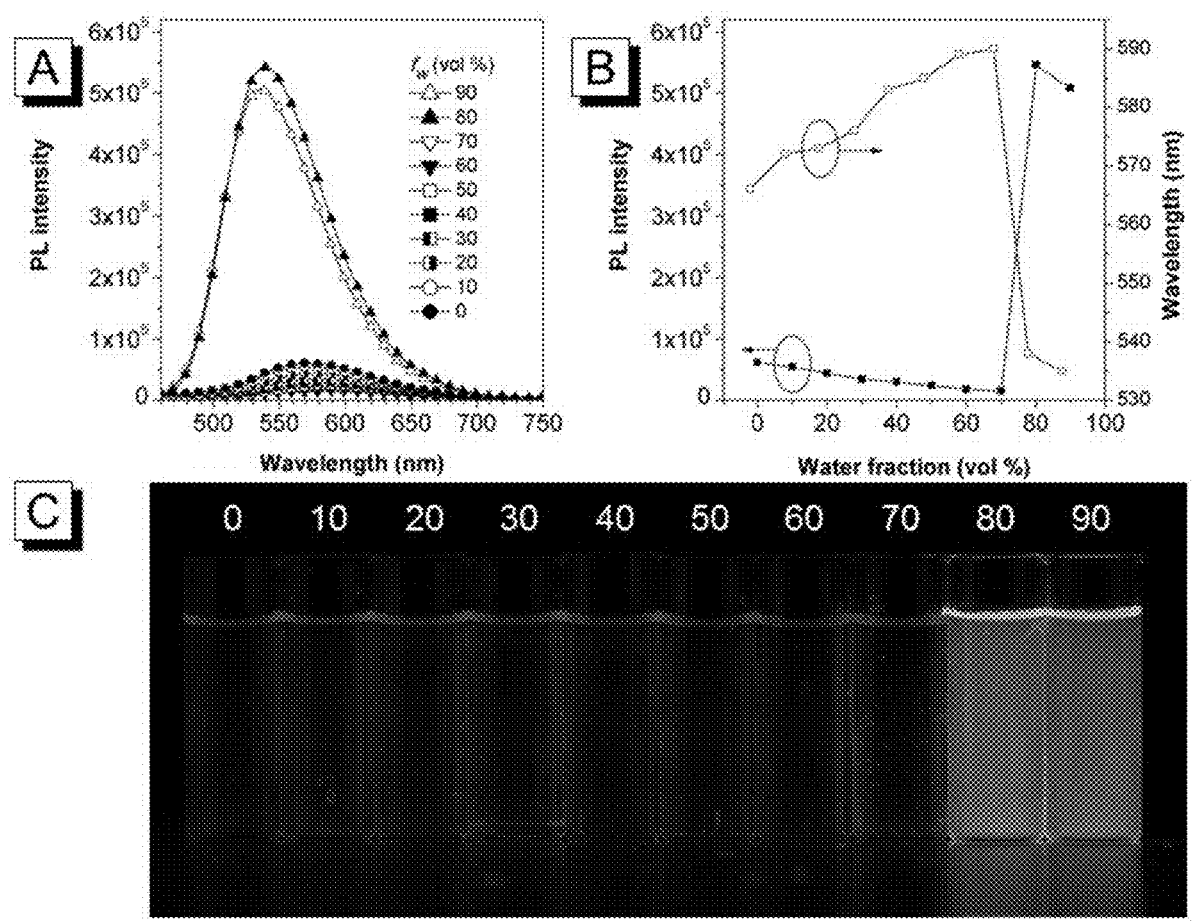
FIG. 10A depicts the PL intensity spectra of different fractions ($f_w$) of DQ1 in methanol/water ($C_{DQ1}$=10 µM).
FIG. 10B depicts a plot of the maximum PL intensity versus the composition of DQ1 methanol/water mixtures.
FIG. 10C depicts luminescence of DQ1 in methanol/water mixtures.
Figures 11A, 11B, 11C:
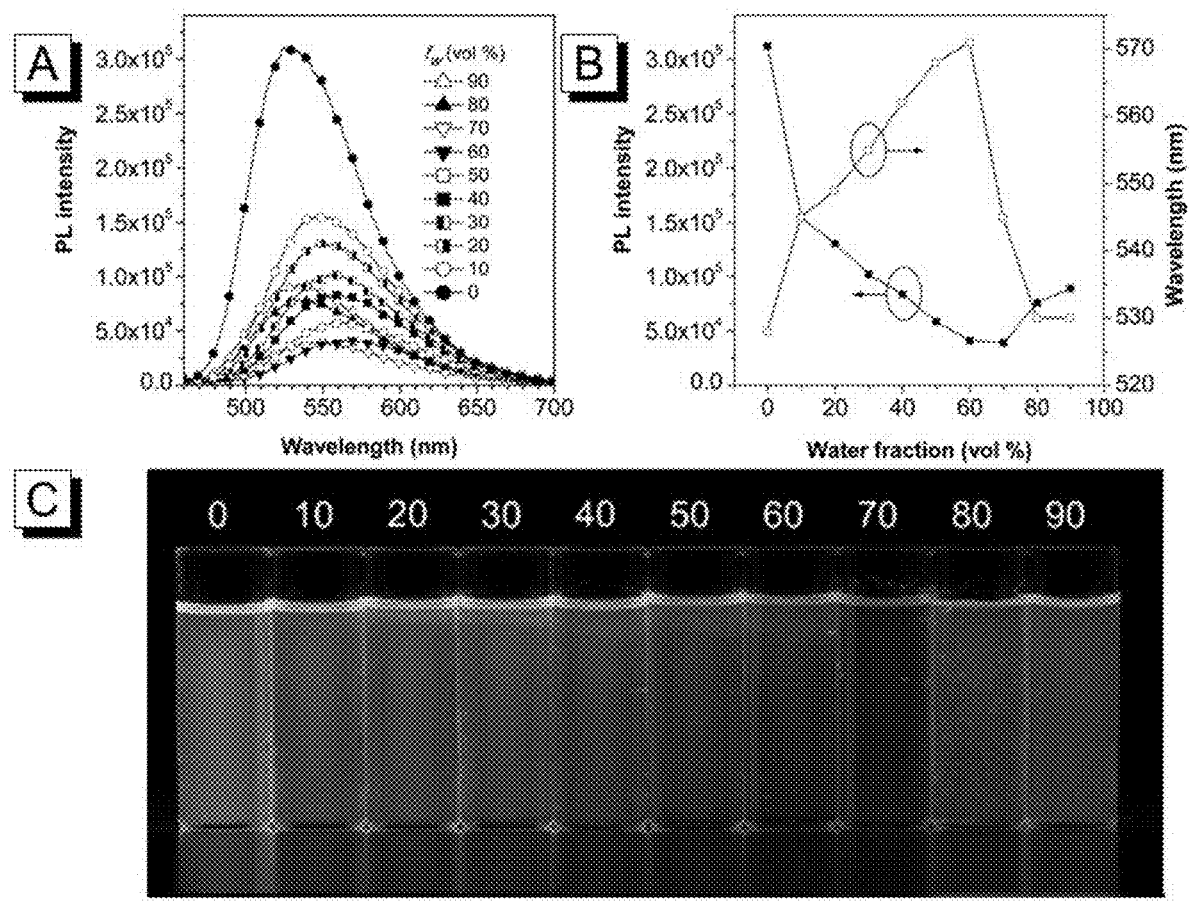
FIG. 11A depicts the PL intensity spectra of different fractions ($f_w$) of DQ1 in tetrahydrofuran (THF)/water ($C_{DQ1}$=10 µM).
FIG. 11B depicts a plot of the maximum PL intensity versus the composition of DQ1 THF/water mixtures.
FIG. 11C depicts luminescence of DQ1 in THF/water mixtures.
Figure 25:
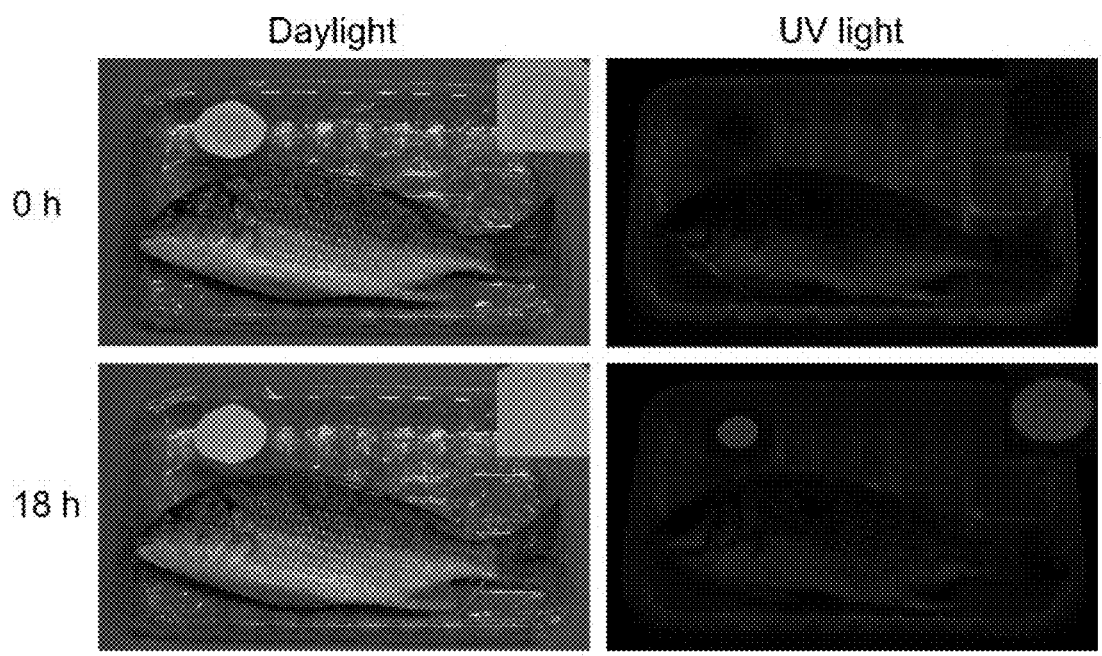
FIG. 25 depicts the H$^+$DQ2 sensor in a sealed package of yellowfin seabream at room temperature for 0 h and 18 h (insets at the top right show magnified views of the sensor strips).
Figure 26:
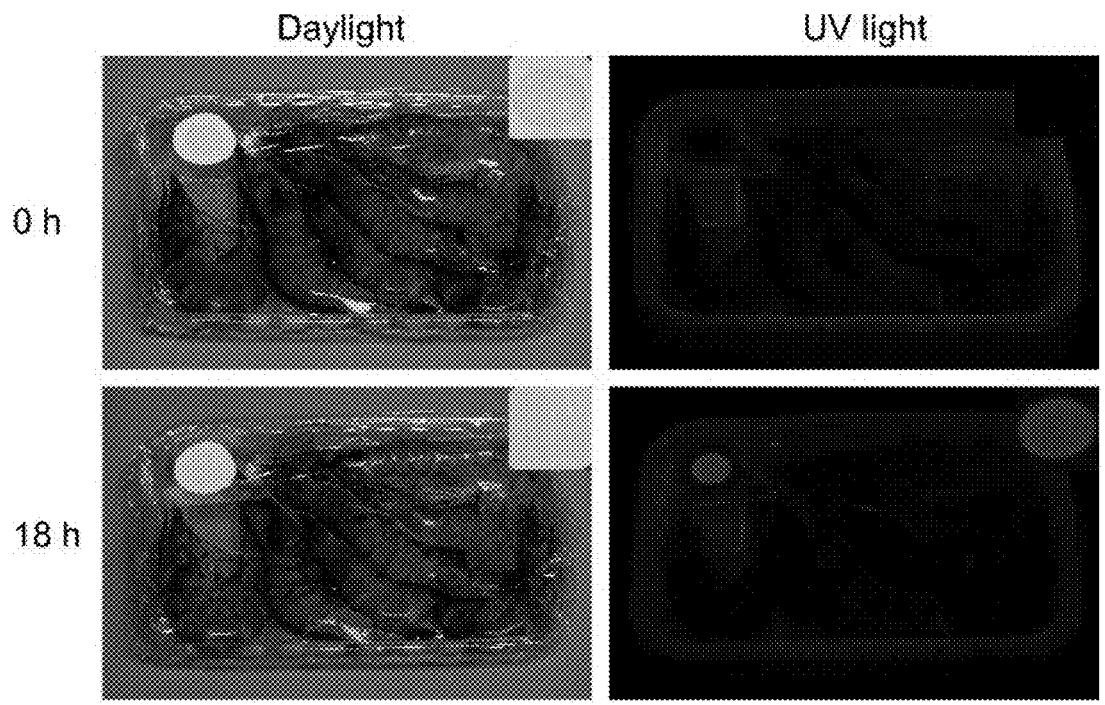
FIG. 26 depicts the H$^+$DQ2 sensor in a sealed package of whiteleg shrimp at room temperature for 0 h and 18 h (insets at the top right show magnified views of the sensor strips).

In an embodiment, the presence of food spoilage in the instant methods is detected by detecting a change in light absorption and/or detecting a change in light emission. In one embodiment, the presence of food spoilage in a sample is detected by a visible color change. The color change can be detected in daylight (FIGS. 9, 25, and 26). FIGS. 25 and 26 show food packages including the AIE chemosensor on a filter paper support. The AIE chemosensor originally displayed a red color under daylight (FIGS. 25 and 26, top left figures). After food fermentation was detected, the visible color changed to yellow (FIGS. 25 and 26, bottom left figures).

According to some embodiments, food fermentation can be detected by both a visible color change and emission activation. For example, the AIE chemosensor $H^+DQ2$ is originally red in color under daylight and is almost non-emissive, with an absorption peak ranging from 400 nm to 600 nm (FIG. 9). Upon food spoilage, the AIE chemosensor becomes deprotonated, forming DQ2. DQ2 is yellow in color under daylight and is brightly emissive, with an absorption peak ranging from 320 nm to 500 nm (FIG. 9). Thus, before food spoilage, the sensor is red/non-emissive, and after food spoilage the sensor is yellow, with yellow emission.

In another embodiment, the presence of food spoilage in a sample is detected by measuring light emission via fluorescence in response to UV excitation. In a further embodiment, the extent of food spoilage in a sample is quantified by observing or measuring emission intensity and noting a change thereof. In this regard, the safety of the food can be determined by observing the emission intensity and noting any changes thereof. For example, deprotonation of the imine nitrogen of the dihydroquinoxaline derivatives upon exposure to the biogenic amines, can produce a detectable change in light absorption and/or a detectable change in light emission. The protonated dihydroquinoxaline derivatives can exhibit weaker emission intensity than unprotonated dihydroquinoxaline derivatives. The emission maximum wavelength of the protonated dihydroquinoxaline derivatives can range from about 560 nm to about 650 nm. The emission maximum wavelength of the unprotonated dihydroquinoxaline derivatives can range from about 500 nm to about 540 nm.

Conventional fluorescent systems include planar aromatic species which suffer from concentration quenching or aggregation caused quenching (ACQ). When rotatable, bulky groups, such as phenyl, triphenyl, or carbazole moieties are introduced, however, the bulky groups rotate and consume excited-state energy in the solution state, making these compounds non-emissive, or weakly emissive, via non-radiative decay processes. However, a contrasting effect is observed in the aggregate or solid state, where emission becomes stronger when the motions of the rotatable groups are hindered. The restriction of intramolecular rotations (RIR) and restriction of intramolecular vibrations (RIV) block non-radiative processes forcing the compounds to luminesce. The incorporation of bulky groups in the compounds helps to prevent $\pi$-$\pi$ stacking interactions, one of the major causes of the ACQ effect. These bulky groups also serve to generate sufficient void space between molecules so that analytes can more easily interact with the AIEgens.

According to some of the present embodiments, addition of acid, e.g., trifluoroacetic acid, can protonate the $sp^2$ nitrogen of the present compounds, resulting in a quenched emission. Addition of amine vapor can deprotonate the nitrogen and restore the bright emission of the original compounds in the solid state. For example, as described herein, the protonated dihydroquinoxaline derivative ($H^+DQ2$) is non-emissive, but quickly becomes emissive after exposure to amines. The non-emissive nature of $H^+DQ2$ is based on self-absorption or the resonance energy transfer (RET) effect, which retards radiative decay through electron transfer from a donor orbital to an acceptor orbital. However, emission intensity returns after exposure to different amines.

Kits

In an embodiment, the present chemosensors, and the methods of using the same, can be delivered via a kit for monitoring food safety, comprising an AIE chemosensor as discussed herein, a filter paper strip; and a packaged food product. In an embodiment, the AIE chemosensor can be loaded onto the filter paper strip as a part of the kit.

The present teachings are illustrated by the following examples.

EXAMPLES

Example 1

Synthesis of Dihydroquinoxaline Derivatives

The present compounds were synthesized by a two-step process: 1) a condensation reaction between diamine and benzil derivatives; and 2) the addition of n-BuLi. Diamine and benzil derivatives were refluxed in the presence of ethanol followed by the addition of n-BuLi in the presence of tetrahydrofuran. An exemplary reaction scheme is provided below:

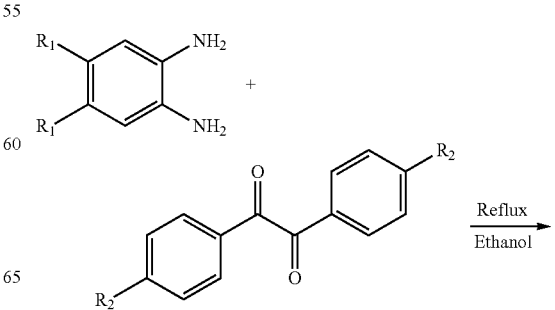

-continued

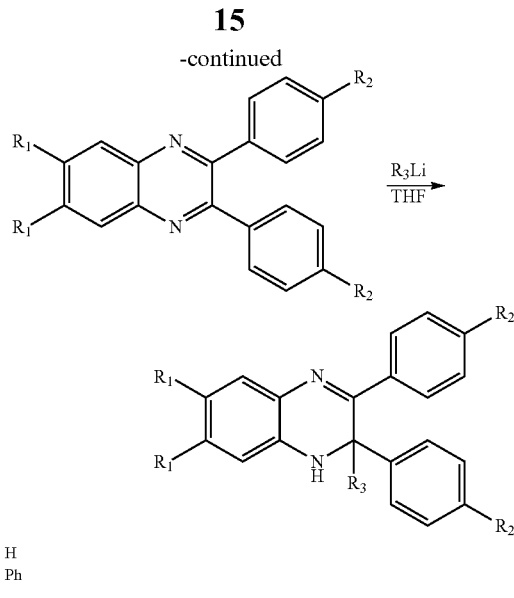

R₁ = Me, H
R₂ = Me, Ph
R₃ = Bu

Example 2

Structure of Dihydroquinoxaline Derivatives

The chemical structures and purity of the dihydroquinoxaline derivative AIE compounds (DQ1, DQ2, DQ3, and DQ4) were confirmed by standard spectroscopic techniques including nuclear magnetic resonance (NRM) and high-resolution mass spectrometry (HRMS). (FIGS. 1A-8).

Example 3

Structure and Optical Properties of DQ2

Figure 2:
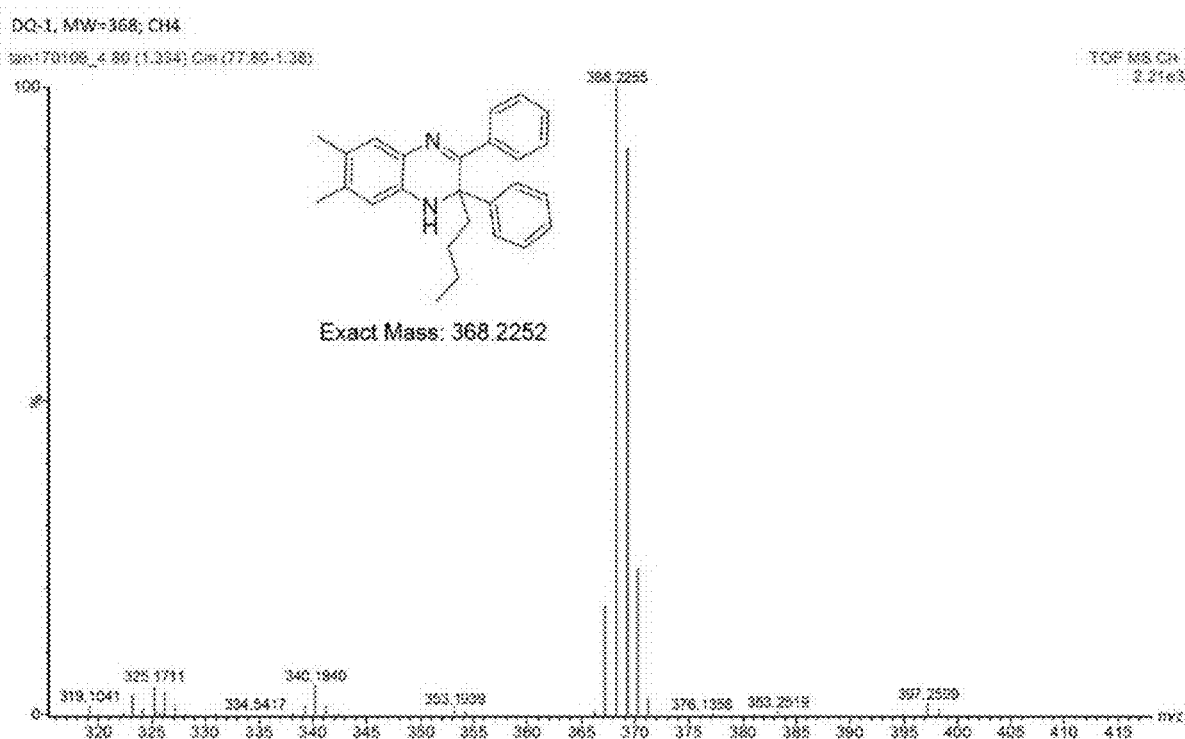
FIG. 2 depicts a high resolution mass spectrum (MALDI-TOF) of DQ1.
Figure 3A:
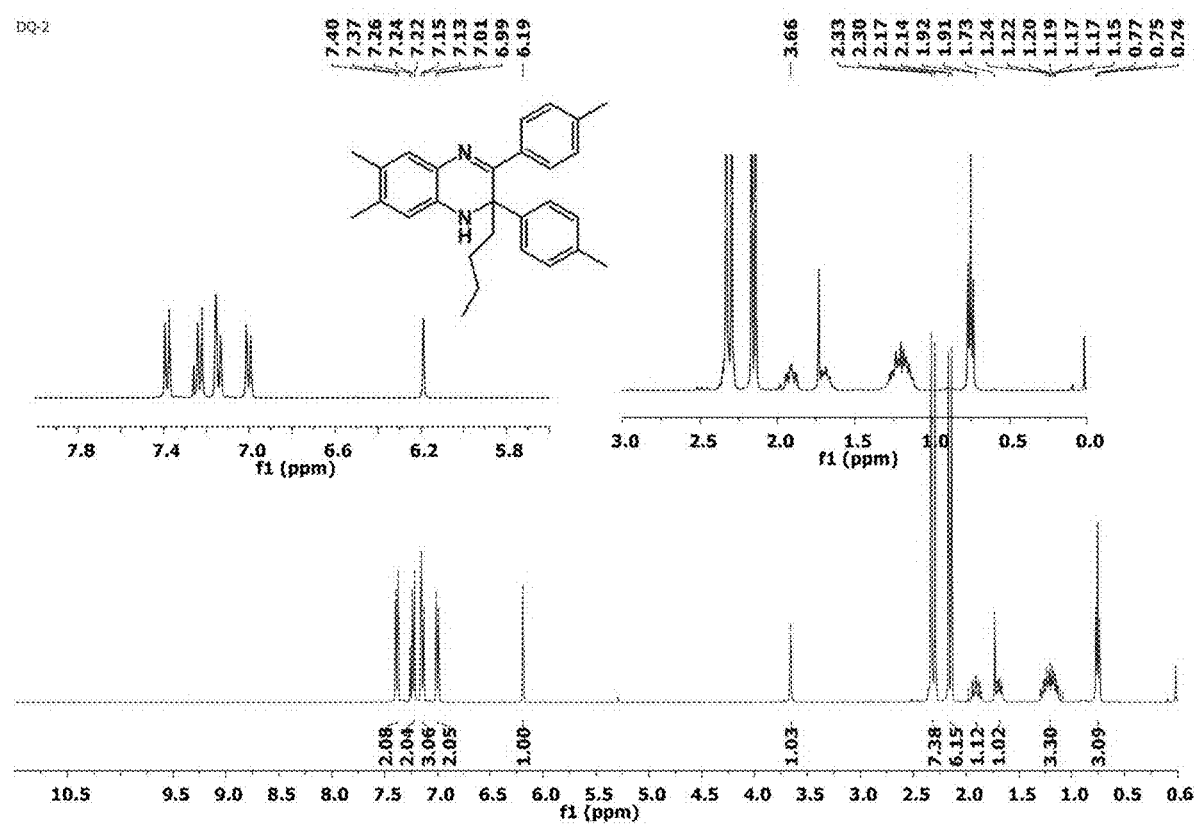
FIG. 3A depicts a $^1$H NMR spectrum of DQ2 in CDCl$_3$.
Figure 3B:
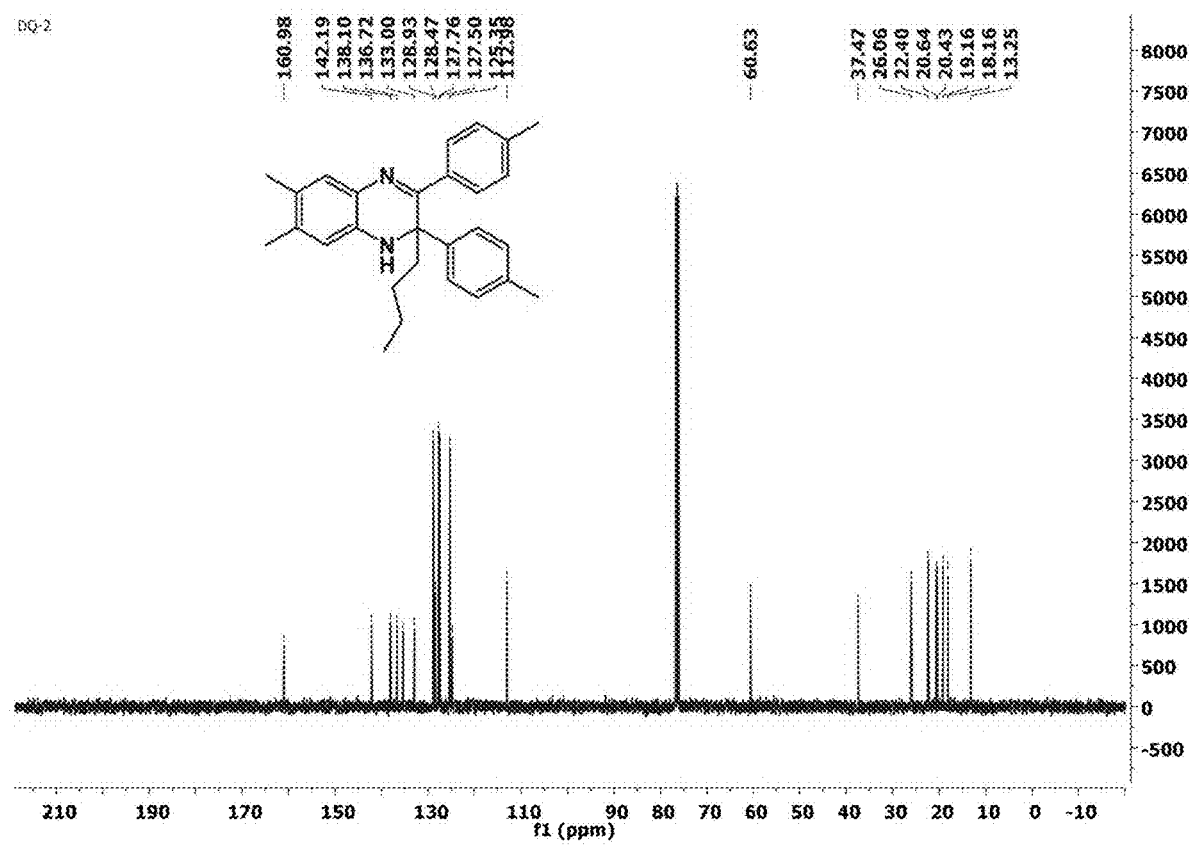
FIG. 3B depicts a $^{13}$C NMR spectrum of DQ2 in CDCl$_3$.
Figure 4:
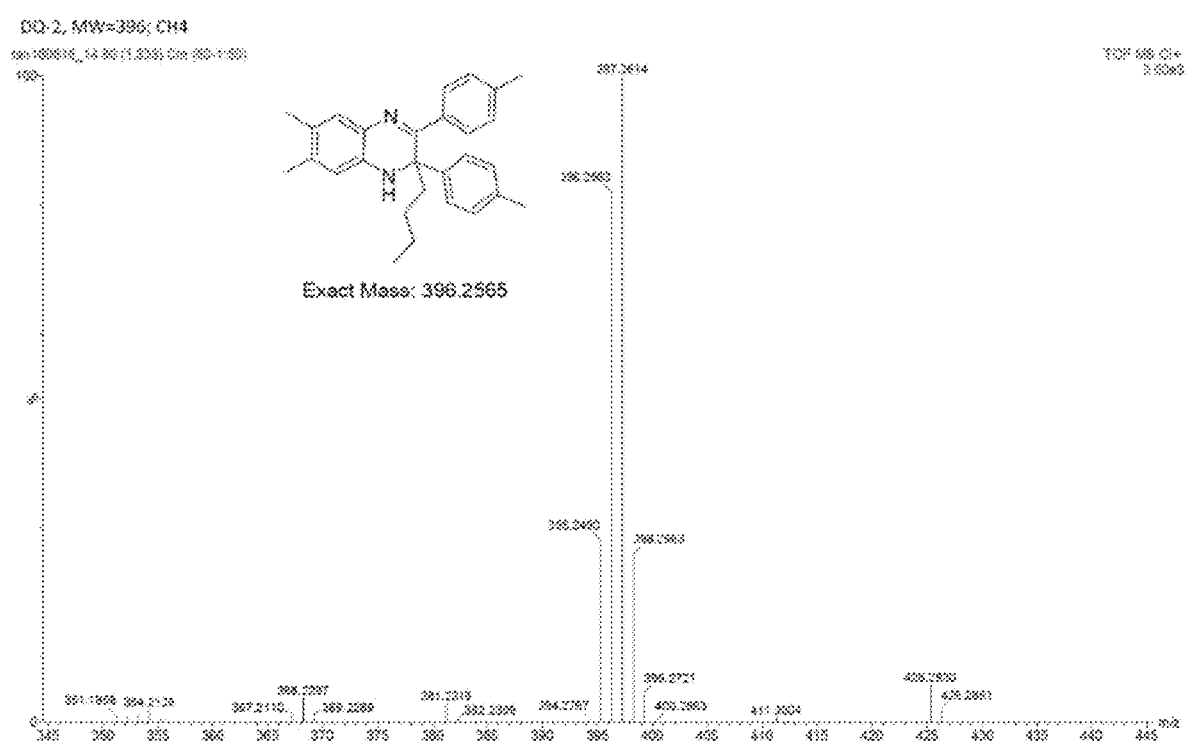
FIG. 4 depicts a high resolution mass spectrum (MALDI-TOF) of DQ2.
Figure 5A:
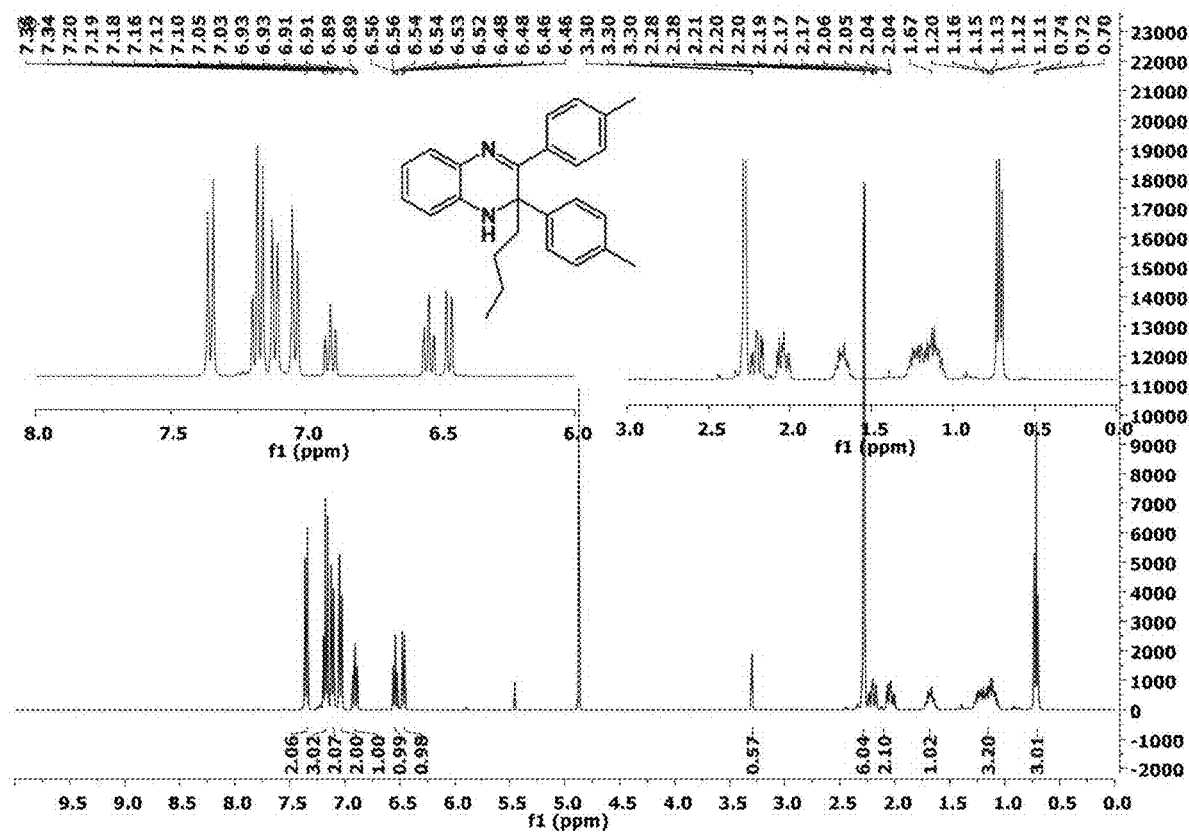
FIG. 5A depicts a $^1$H NMR spectrum of DQ3 in CDCl$_3$.
Figure 5B:
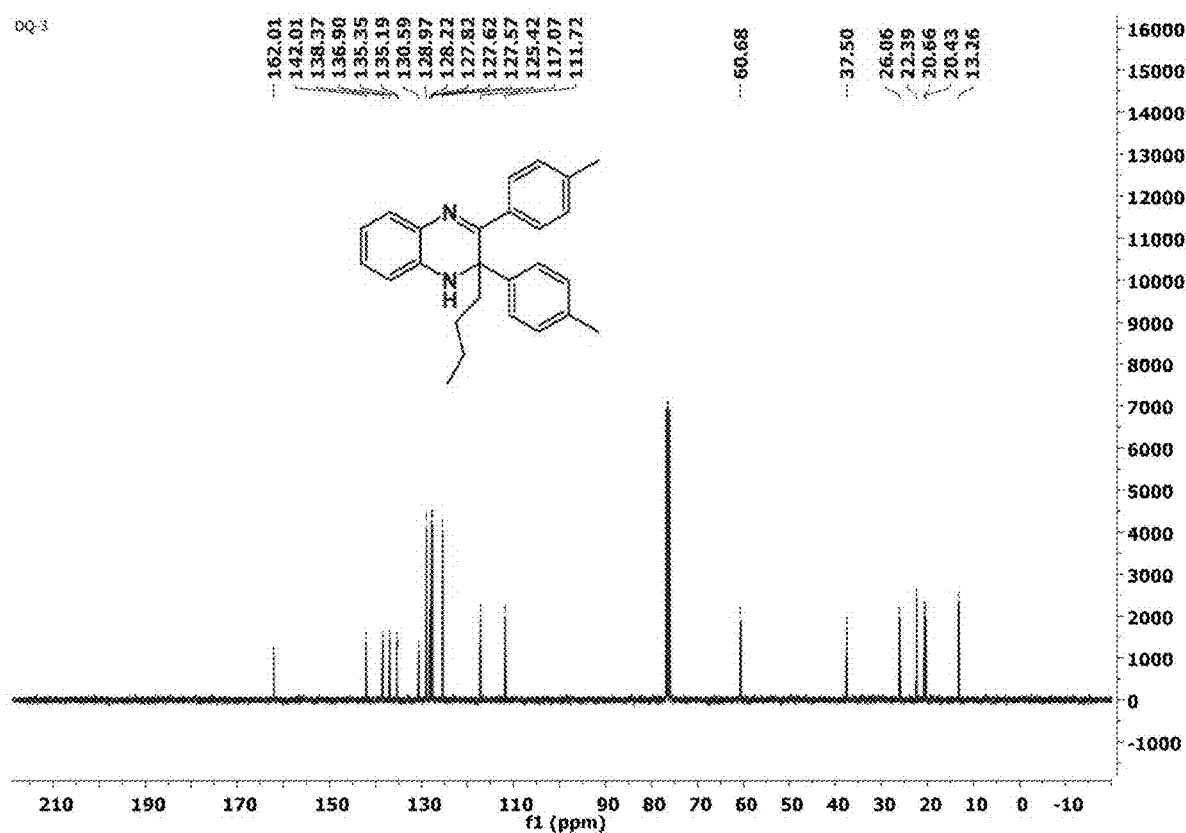
FIG. 5B depicts a $^{13}$C NMR spectrum of DQ3 in CDCl$_3$.
Figure 6:
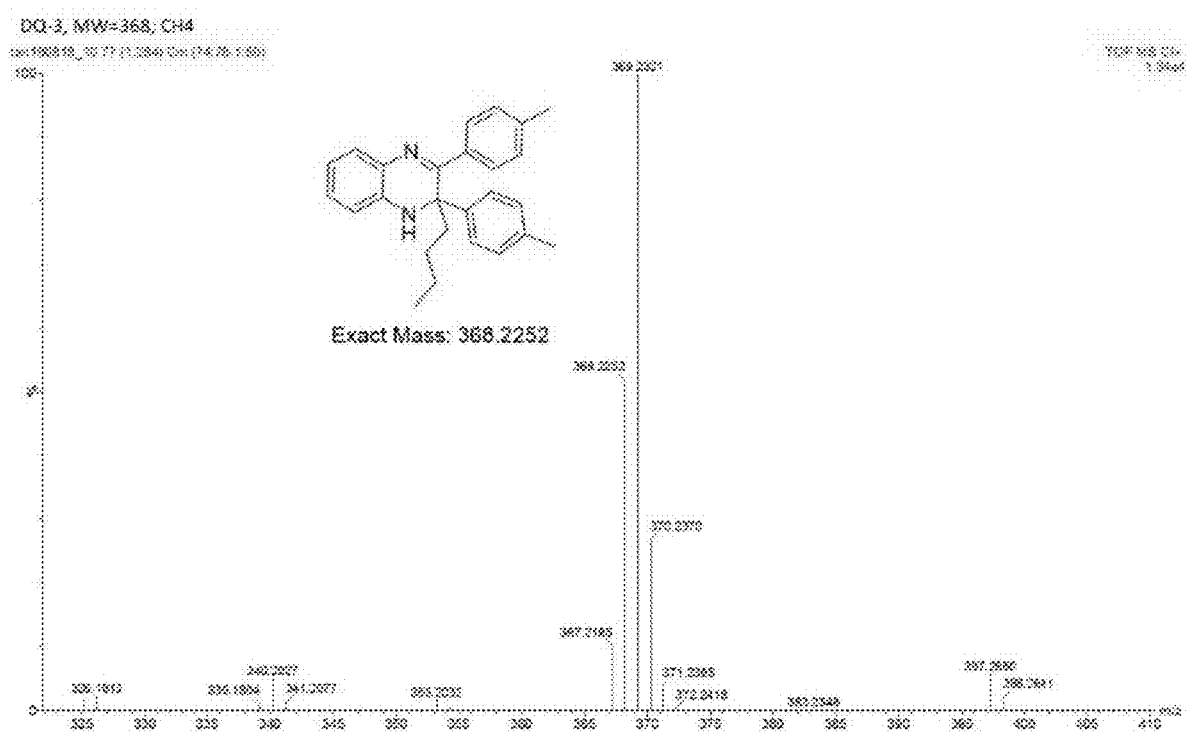
FIG. 6 depicts a high resolution mass spectrum (MALDI-TOF) of DQ3.
Figure 7A:
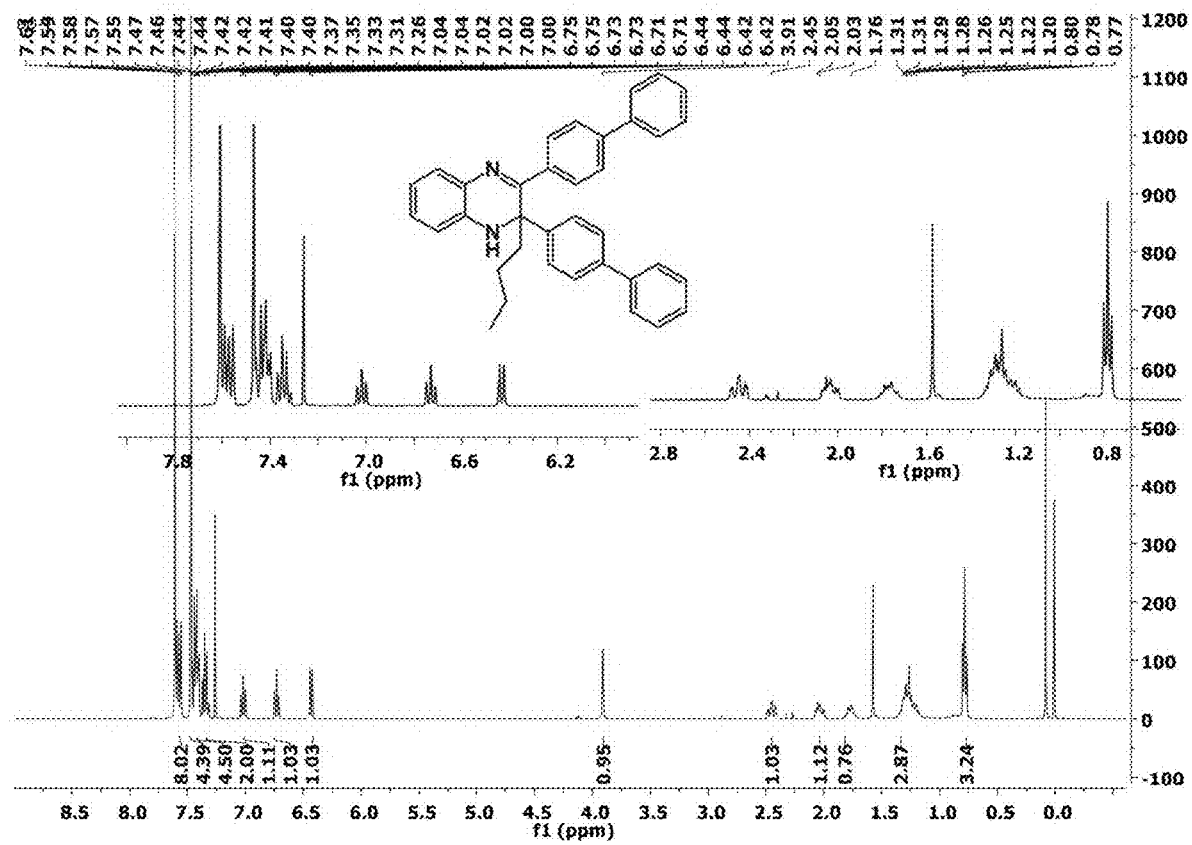
FIG. 7A depicts a $^1$H NMR spectrum of DQ4 in CDCl$_3$.
Figure 7B:
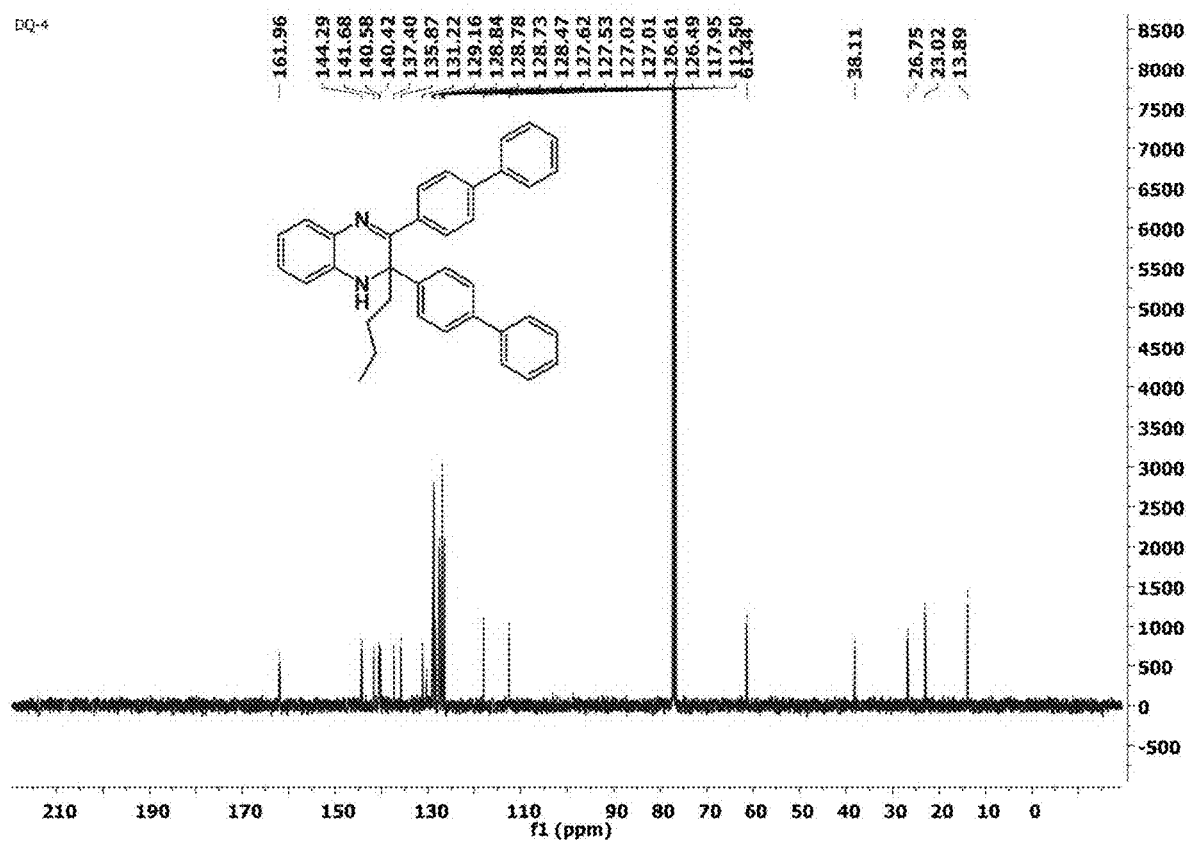
FIG. 7B depicts a $^{13}$C NMR spectrum of DQ4 in CDCl$_3$.
Figure 8:
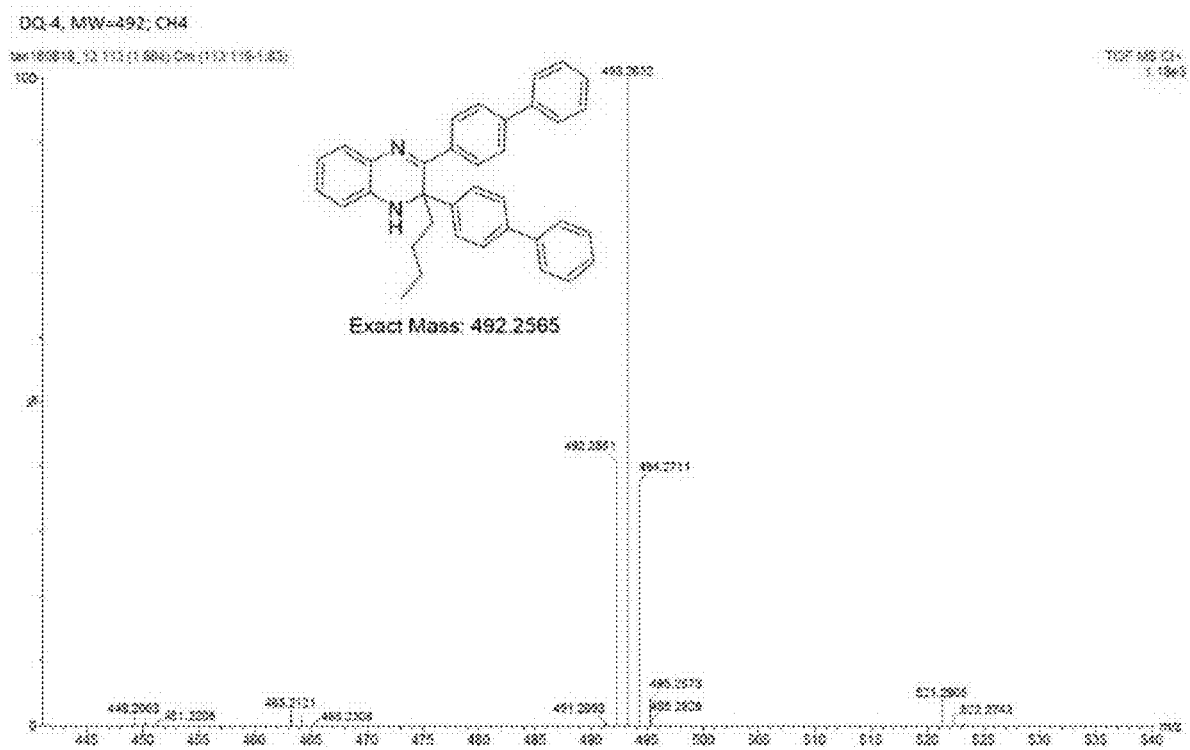
FIG. 8 depicts a high resolution mass spectrum (MALDI-TOF) of DQ4.

DQ2 was produced according to the method of Example 1. The purity and identity of DQ2 was confirmed by $^1$H NMR (FIG. 1A), $^{13}$C NMR (FIG. 1B) and HRMS (FIG. 2). Protonated DQ2 (H$^+$DQ2) was produced by reacting DQ2 with trifluoroacetic acid (TFA).

The optical properties (absorption and emission spectra) of DQ2 were recorded in different organic solvents (polar and non-polar) at room temperature. The absorption spectra of DQ2 in dichloromethane (DCM) showed two peaks at 270 nm and 392 nm, and after the addition of TFA (100 μM) to form H$^+$DQ2, the peaks changed to 338 nm and 478 nm, respectively (FIG. 9).

Example 4

AIE Properties of Dihydroquinoxaline Derivatives

Figures 12A, 12B, 12C:
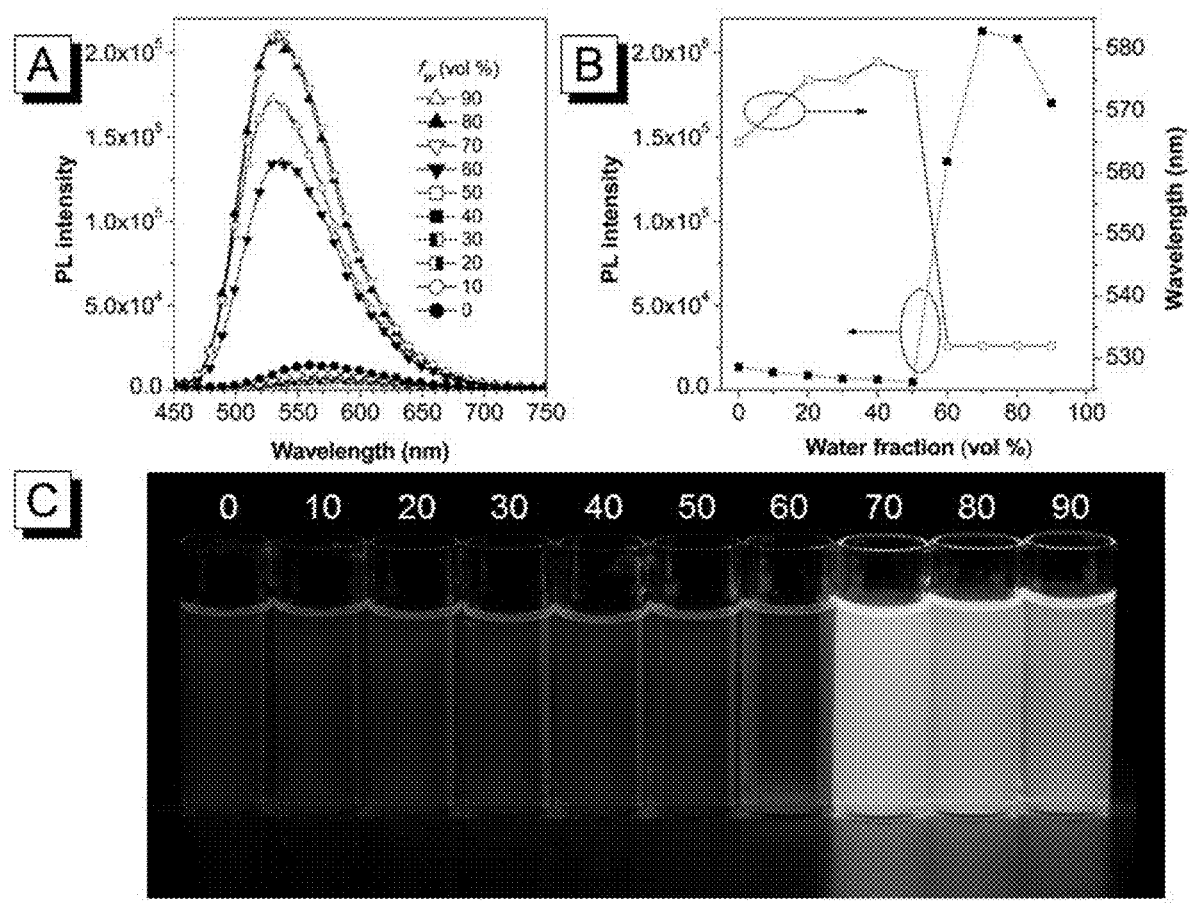
FIG. 12A depicts the PL intensity spectra of different fractions ($f_w$) of DQ2 in methanol/water ($C_{DQ2}$=10 µM).
FIG. 12B depicts a plot of the maximum PL intensity versus the composition of DQ2 methanol/water mixtures.
FIG. 12C depicts luminescence of DQ2 in methanol/water mixtures.
Figures 13A, 13B, 13C:
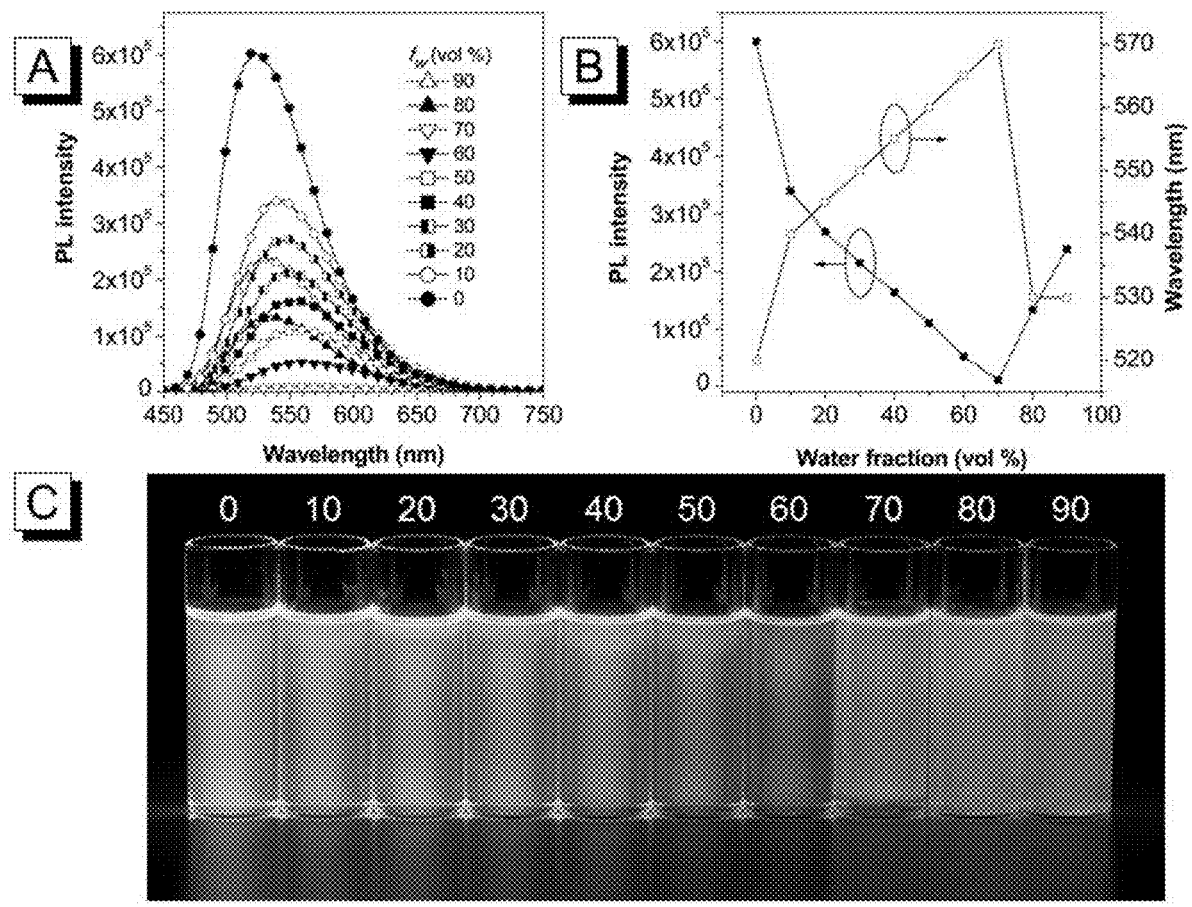
FIG. 13A depicts the PL intensity spectra of different fractions ($f_w$) of DQ2 in THF/water ($C_{DQ2}$=10 µM).
FIG. 13B depicts a plot of the maximum PL intensity versus the composition of DQ2 THF/water mixtures.
FIG. 13C depicts luminescence of DQ2 in THF/water mixtures.
Figures 14A, 14B, 14C:
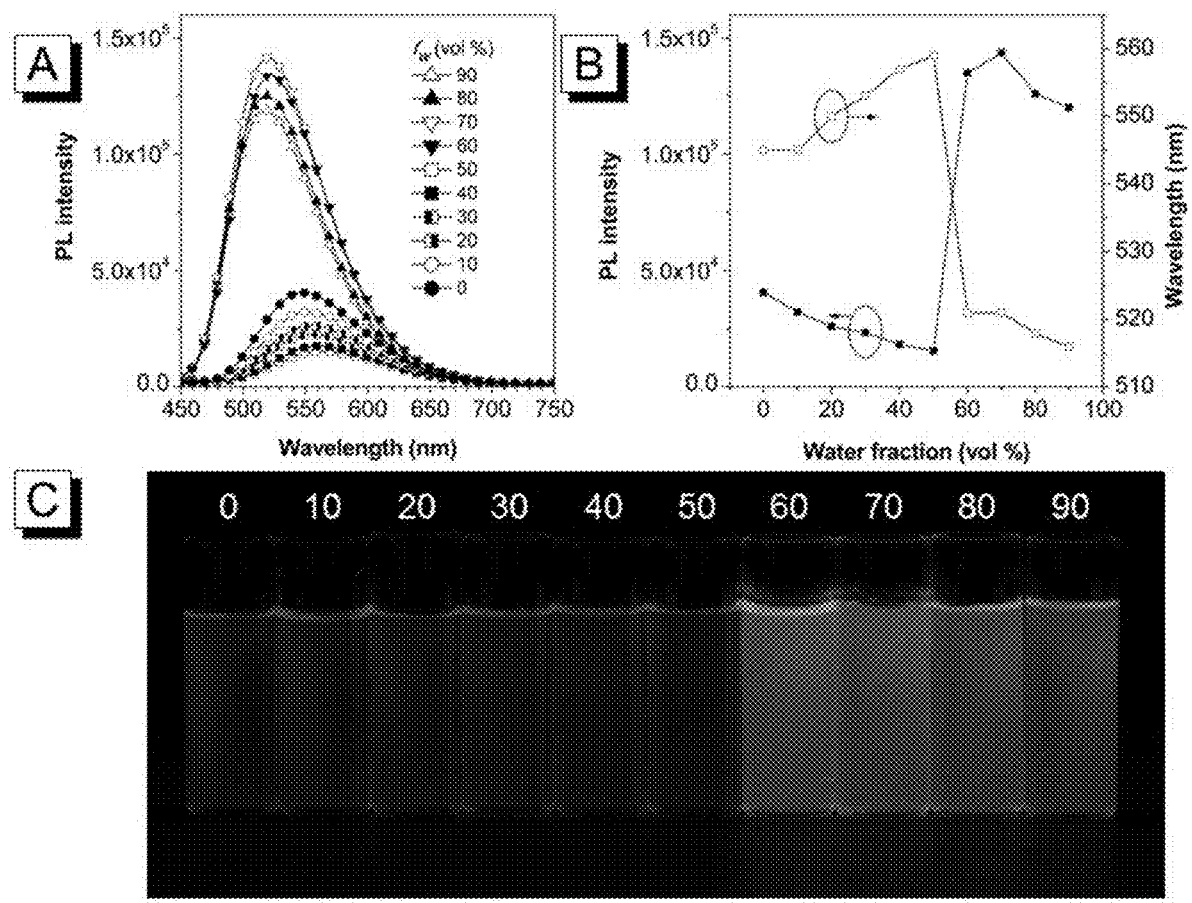
FIG. 14A depicts the PL intensity spectra of different fractions ($f_w$) of DQ3 in methanol/water ($C_{DQ3}$=10 µM).
FIG. 14B depicts a plot of the maximum PL intensity versus the composition of DQ3 methanol/water mixtures.
FIG. 14C depicts luminescence of DQ3 in methanol/water mixtures.
Figures 15A, 15B, 15C:
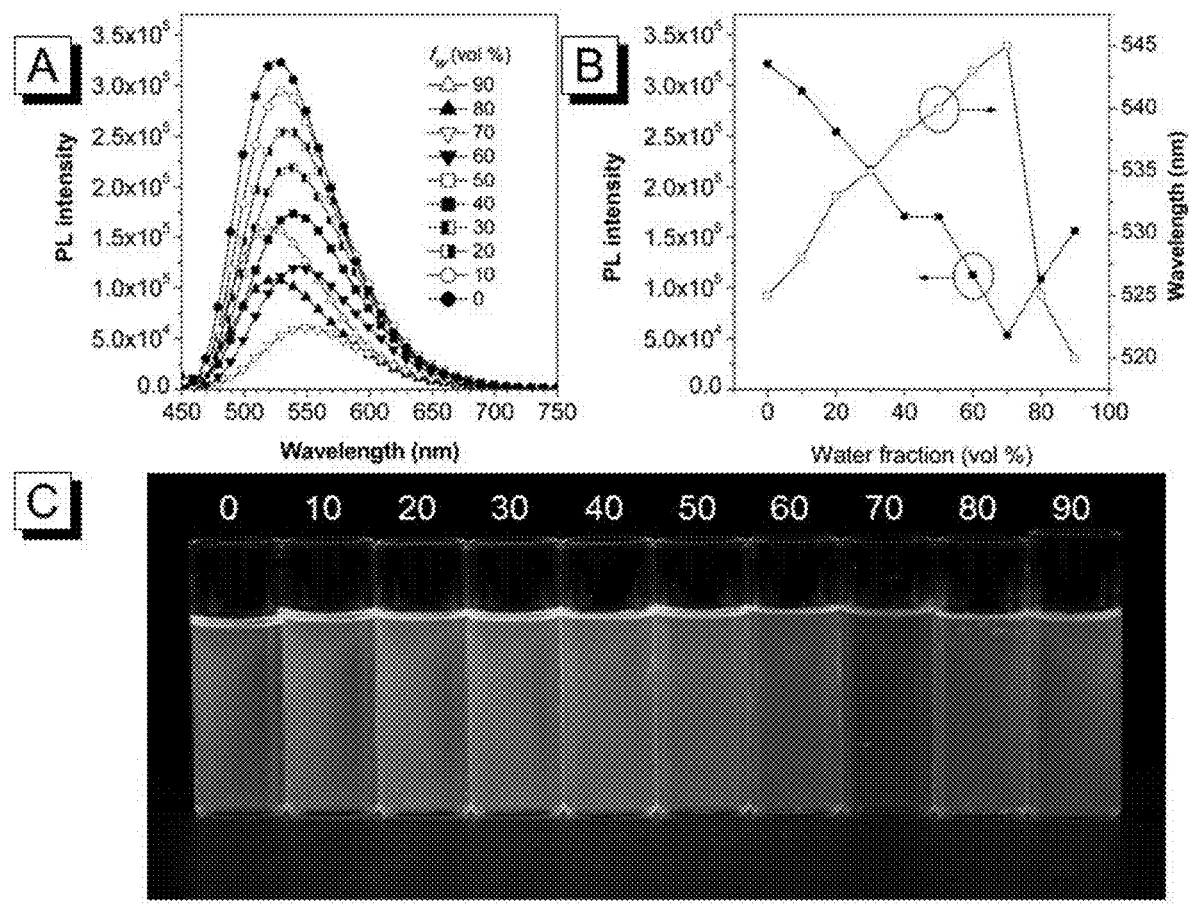
FIG. 15A depicts the PL intensity spectra of different fractions ($f_w$) of DQ3 in THF/water ($C_{DQ3}$=10 µM).
FIG. 15B depicts a plot of the maximum PL intensity versus the composition of DQ3 THF/water mixtures.
FIG. 15C depicts luminescence of DQ3 in THF/water mixtures.
Figures 16A, 16B, 16C:
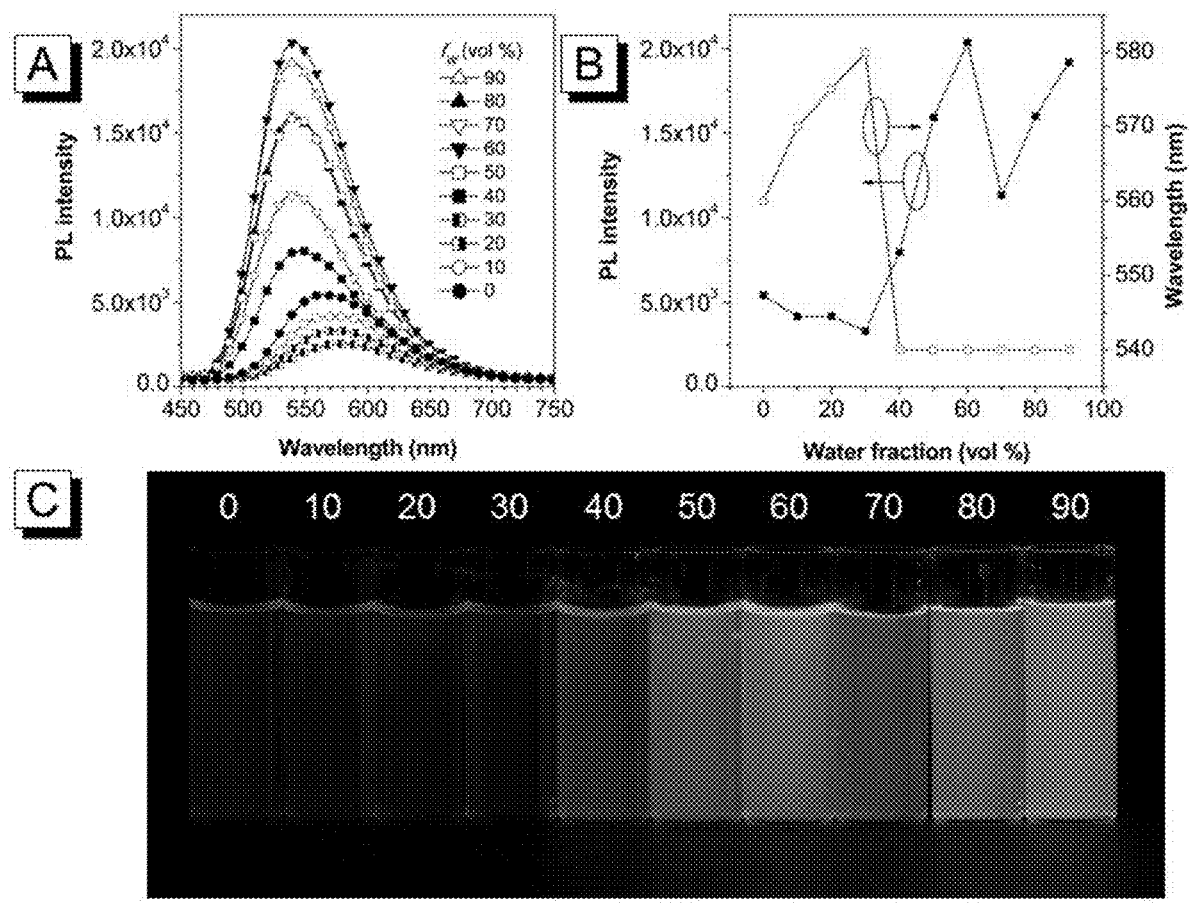
FIG. 16A depicts the PL intensity spectra of different fractions ($f_w$) of DQ4 in methanol/water ($C_{DQ4}$=10 µM).
FIG. 16B depicts a plot of the maximum PL intensity versus the composition of DQ4 methanol/water mixtures.
FIG. 16C depicts luminescence of DQ4 in methanol/water mixtures.
Figures 17A, 17B, 17C:
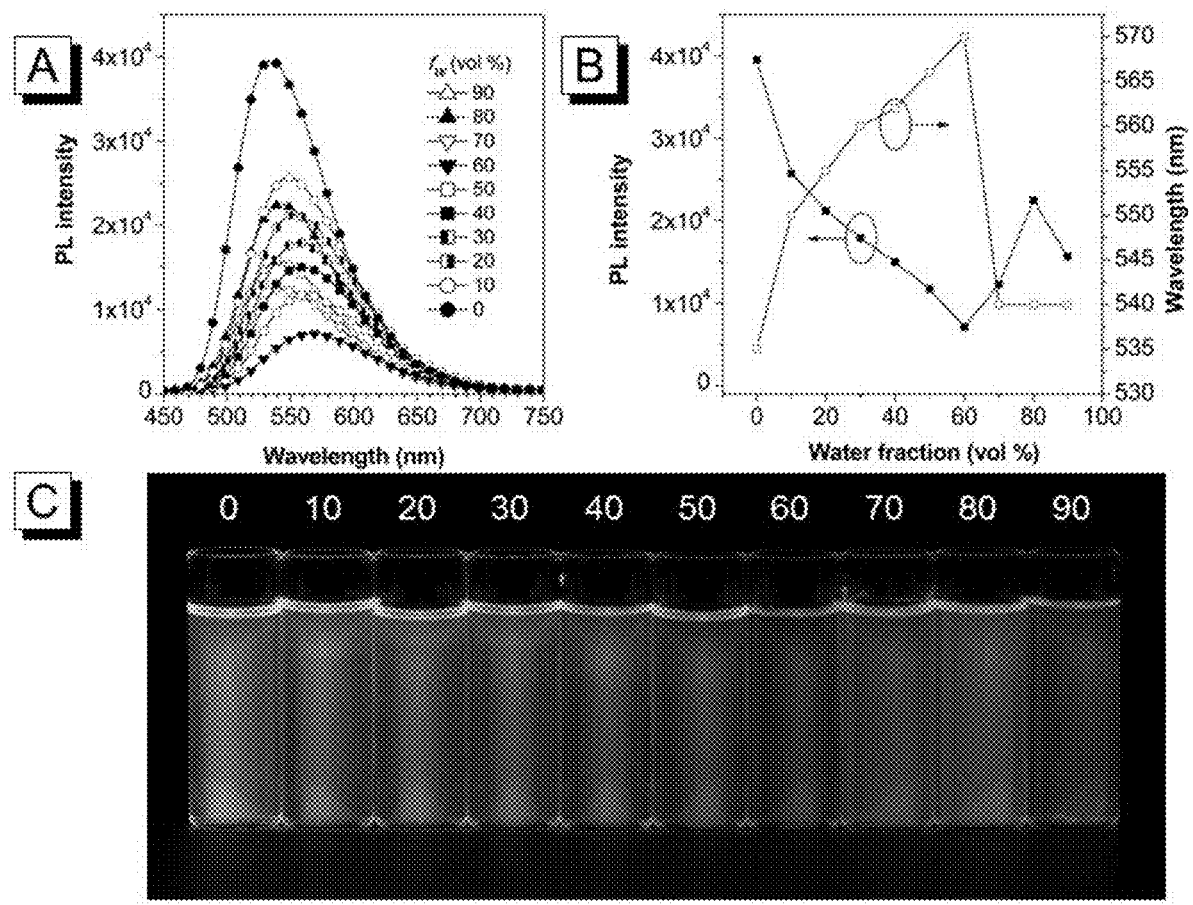
FIG. 17A depicts the PL intensity spectra of different fractions ($f_w$) of DQ4 in THF/water ($C_{DQ4}$=10 µM).
FIG. 17B depicts a plot of the maximum PL intensity versus the composition of DQ4 THF/water mixtures.
FIG. 17C depicts luminescence of DQ4 in THF/water mixtures.

The AIE properties of DQ1-DQ4 were further studied in two different solvents systems: (a) methanol/water (FIGS. 10A-10C, 12A-12C, 14A-14C, and 16A-16C) and (b) THF/water mixtures (FIGS. 11A-11C, 13A-13C, 15A-15C and 17A-17C). For DQ2, increasing water fraction ($f_w$) in the methanol/water mixture (varying from 0 to 60%) resulted in a gradual diminution in emission alongside a bathochromic shift (from 573 nm to 585 nm) (FIGS. 12A-12C). The gradual addition of water dramatically weakened the photoluminescence (PL) intensity with a bathochromic shift, due to the increase in solvent polarity and to properties related to intramolecular charge transfer (ICT) of DQ2. ICT properties can include, for example, absorption maximum, emission maximum, and/or emission intensity change depending on the polarity of the environment. However, at $f_w$=70%, an immediate 28-fold enhancement was observed with a hypsochromic shift (538 nm) in the PL spectra. Further addition of water $f_w$≥70% resulted in an enhanced blue shifted emission due to nanoaggregate formation. The PL intensity enhancement at $f_w$=70% is indicative of AIE activity. Hence DQ2 exhibits both AIE and ICT properties. Similar AIE behavior was observed for other DQ molecules in presence of different methanol/water and THF/water mixtures. Specifically, the emission of DQs in polar solvents red-shifts (bathochromic shifts) and significantly weakens. In non-polar environments, the emission of DQs blue-shifts (hypsochromic shifts) and is enhanced.

Example 5

AIE Properties of Protonated and Deprotonated DQ2

Figure 18:
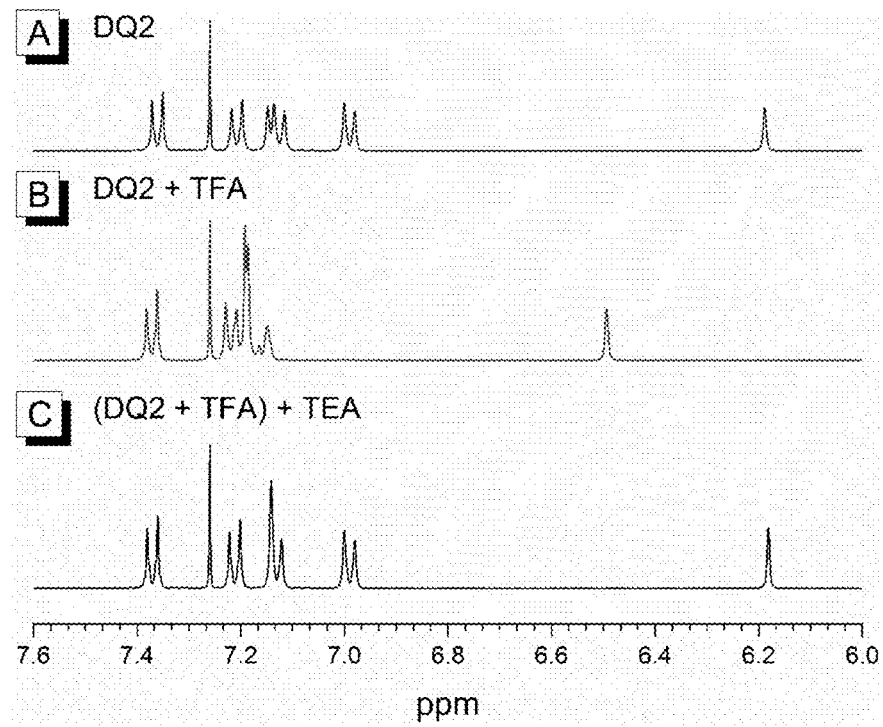
FIGS. 18A-18C depicts the NMR spectra of DQ2 (FIG. 18A), DQ2 in the presence of trifluoroacetic acid (TFA) (FIG. 18B), and DQ2 in the presence of TFA and triethylamine (TEA) (FIG. 18C).
Figure 19:
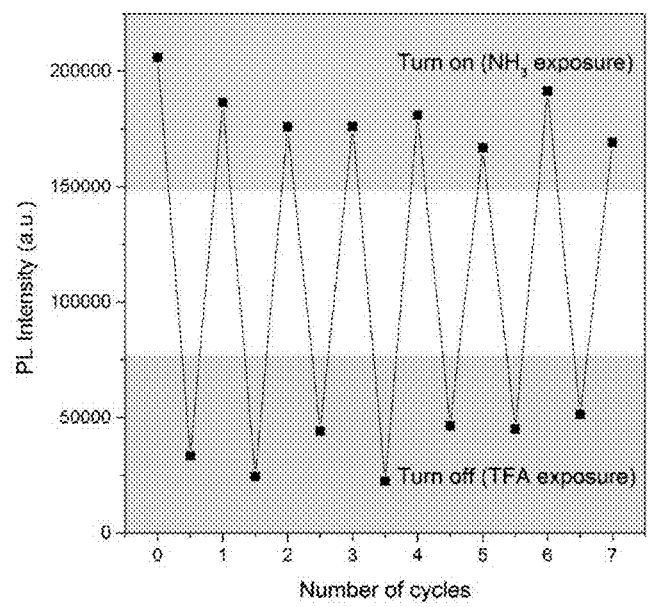
FIG. 19 depicts PL intensity at 530 nm of H$^+$DQ2 filter paper strips after repeated cycling exposure to ammonia vapor and TFA.

The PL spectra showed a similar result where the emission maxima of DQ2 red shifted from 530 nm to 560 nm (FIG. 9). However, the addition of base (Et$_3$N; triethylamine (TEA)), resulted in restoration of the emission peak at 530 nm. The measurements were done in DCM solution, however, the color change in absorbance was visible in other solvents and in the solid state. This process was also monitored using NMR spectroscopy (FIG. 18A-18C). After the addition of trifluoroacetic acid TFA (FIG. 18B), the original peak at 6.18 shifted to 6.50; upon deprotonation with TEA (FIG. 18C), the peak returned to 6.18. These experiments show the protonation and deprotonation of DQ2 is reversible in nature. To further examine the reversibility of the system, H$^+$DQ2 was loaded onto filter paper and multiple cycles of exposure to NH$_3$ and TFA were recorded (FIG. 19). H$^+$DQ2 initially shows no emission; however, emission is activated by exposure to ammonia gas and deactivated by exposure to TFA. The system further demonstrates reversibility and repeatability over multiple NH$_3$/TFA exposure cycles.

Example 6

H$^+$DQ2 Activation Sensitivity

Figure 20A:
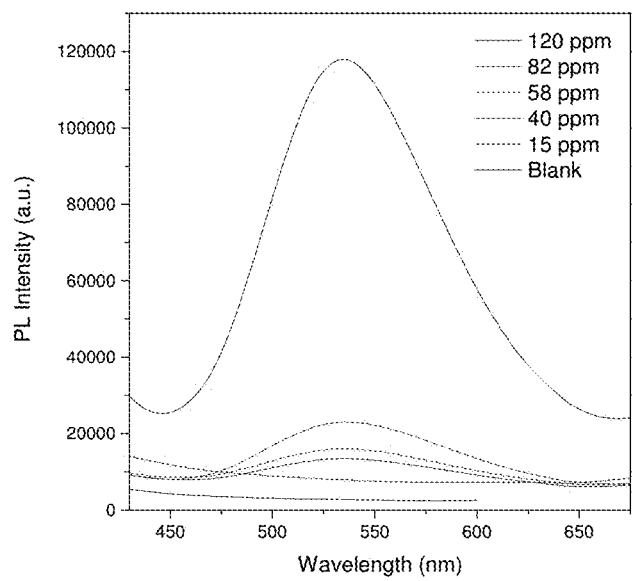
FIG. 20A depicts the PL spectra of H$^+$DQ2 filter paper strips after 5 min exposure to 0 ppm, 15 ppm, 40 ppm, 58 ppm, 82 ppm, and 120 ppm of ammonia vapor.
Figure 20B:
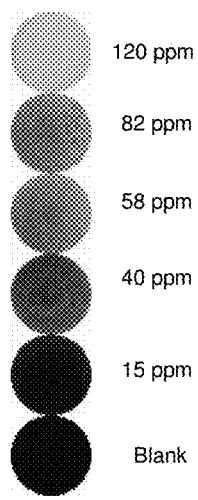
FIG. 20B depicts photographs of the H$^+$DQ2 filter paper strips after exposure to ammonia vapor under UV excitation at 365 nm.
Figure 21:
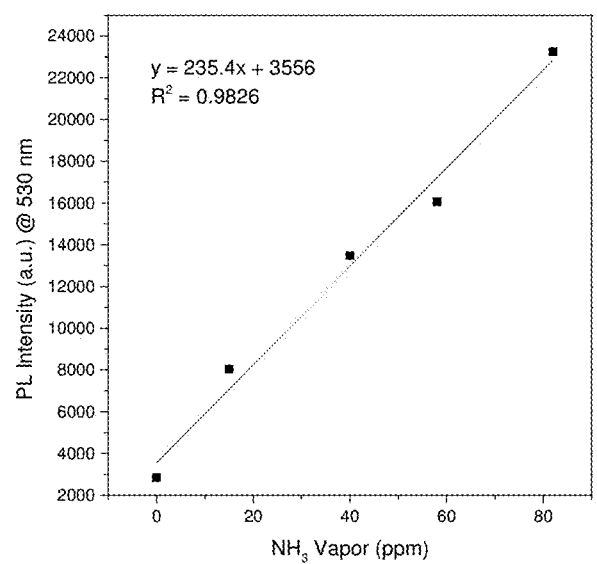
FIG. 21 depicts a graph of PL intensities of H$^+$DQ2 filter paper strips after exposure to 0 ppm, 15 ppm, 40 ppm, 58 ppm, and 82 ppm of ammonia vapor (UV excitation at 530 nm).

H$^+$DQ2 filter paper strip activation sensitivity was examined by exposing the strips to various concentrations of NH$_3$ vapor (concentrations from about 15 ppm to about 120 ppm). 5 mL of about 15 ppm, about 40 ppm, about 58 ppm, about 82 ppm, and about 120 ppm of NH$_3$ solution were placed in 100 mL bottles which were sealed overnight to allow the NH$_3$ vapor to equilibrate. NH$_3$ vapor concentrations were measured using Gastec detector tubes and the activated emissions were measured using photoluminescence spectroscopy (FIG. 20A). Photographs of these filter paper strips were taken after exposure to the ammonia vapor and UV excitation at 365 nm (FIG. 20B). The limit of detection was then calculated to be 635 ppb from the regression line using the PL intensity at 530 nm versus the ppm concentration using the equation 3σ/m, where σ is the standard deviation of the blank measurement and m is the calculated regression slope (FIG. 21).

Example 7

Fluorescence Detection of Biogenic Amines

A portable DQ2 chemosensor was prepared by dropwise application of a 100 μM DCM solution of H$^+$DQ2 onto a strip of filter paper. The portable DQ2 chemosensor can be used after the evaporation of solvent. The reversibility of the sensor was confirmed by exposing the strip to TFA and ammonia vapors, sequentially (FIG. 19).

Figure 22:
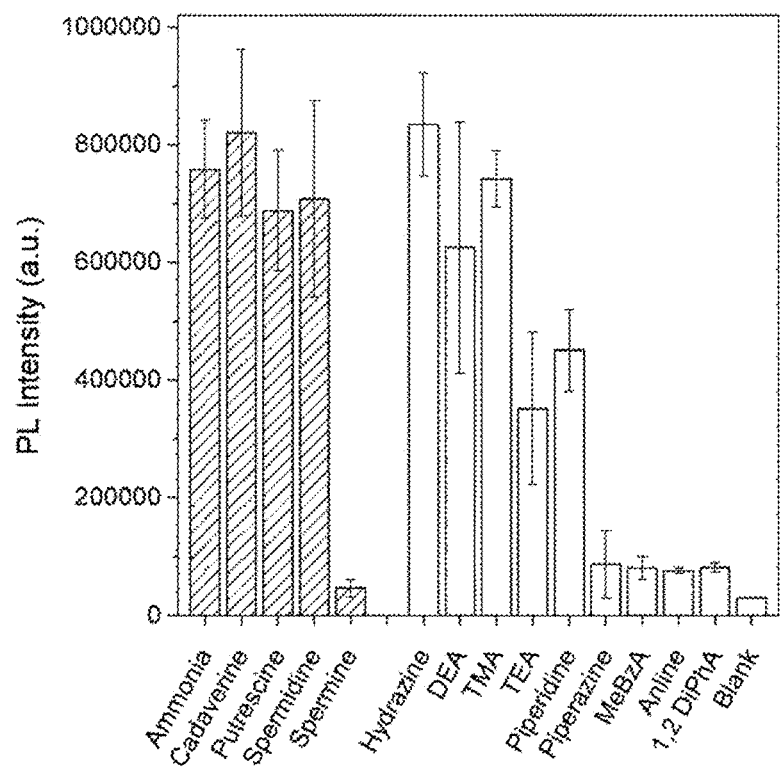
FIG. 22 depicts a graph of PL turn-on response of H$^+$DQ2 filter paper strips in the presence of various amine vapors (UV excitation at 510 nm; DEA=diethylamine; TMA=trimethylamine; TEA=triethylamine; MeBzA=methylbenzylamine; 1,2 DiPhA=1,2-diphenylamine).

The fluorescence activation capability of the H⁺DQ2 chemosensor was investigated using different amine vapors. 10 mL of 0.08 M methanol solutions of hydrazine, diethylamine (DEA), trimethylamine (TMA), triethylamine (TEA), piperidine, piperazine, methylbenzylamine (MeBzA), aniline, 1,2-diphenylamine (1,2 DiPhA), cadaverine, putrescine, spermidine, and spermine were prepared in 25 mL glass vials. Prior to exposure to the amine vapors, the DQ2 chemosensors showed minimal fluorescence signal at 530 nm. They were then placed on top of the open glass vials of the methanol amine solutions for 40 seconds. After exposure to the amine solutions, the fluorescence of the DQ2 chemosensors was measured. The first detection cycle was then concluded by exposing the DQ2 chemosensors to TFA vapor to be reprotonated. A total of three detection cycles were completed for each amine solution and the PL responses were graphed (FIG. 22). The DQ2 chemosensors showed an activation response within 40 seconds after exposure to ammonia, cadaverine, putrescine, spermidine along with hydrazine, TEA, DEA, TMA and piperidine. Less volatile amine species such as spermine, piperazine, MeBzA, aniline, and 1,2 DiPhA showed weaker activation.

These experiments demonstrate the potential of DQ2 chemosensors as activated fluorescence sensors for volatile amines, including important biogenic amines (BAs).

Example 8

Detection of Amines from Food Samples

Figure 23:
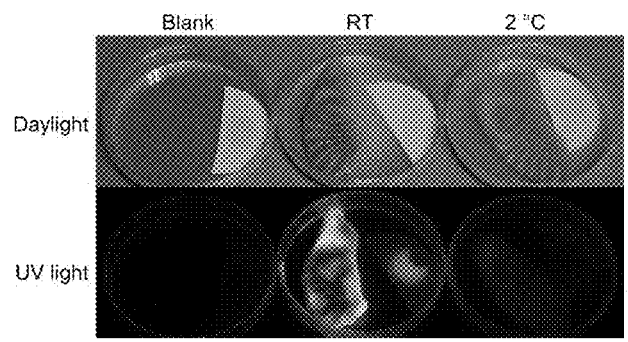
FIG. 23 depicts photographs of blank controls, raw salmon (sashimi) kept at room temperature, and raw salmon (sashimi) kept at 2° C. for 48 hours under daylight conditions and UV excitation.

Based on the results of DQ2 chemosensors for detecting biogenic amines, further testing was performed of their capacity to detect food spoilage. Fresh samples of salmon sashimi, yellowfin seabream, and whiteleg shrimp were purchased from a local supermarket. Three sealed Petri dishes with DQ2 chemosensors were prepared: i) a blank as a control; ii) a sample of salmon sashimi kept at room temperature (RT); and iii) a sample of salmon sashimi kept at 2° C. (FIG. 23). After 48 hours, the only DQ2 chemosensor to show any change was the DQ2 chemosensor sealed with the sashimi sample kept at room temperature. The originally red color changed to yellow and emission activation was observed. The control DQ2 chemosensor and the DQ2 chemosensor kept with the sashimi sample at 2° C. showed no color change and remained non-emissive.

Figure 24:
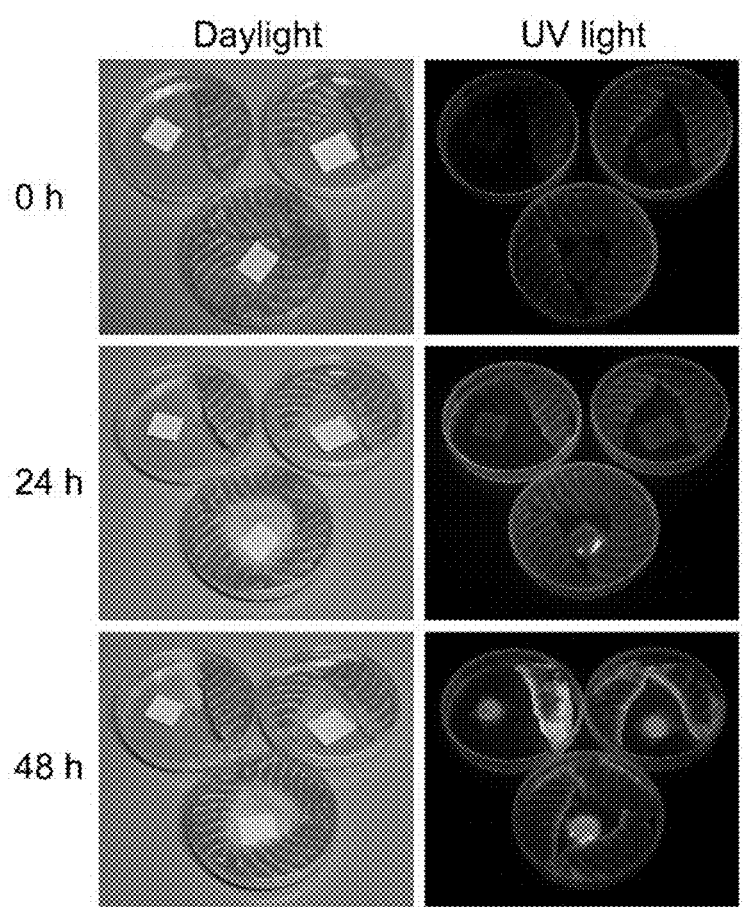
FIG. 24 depicts the H$^+$DQ2 sensor sealed with raw salmon (sashimi) at room temperature for 0 h, 24 h, and 48 h under daylight and UV light.

Further testing of the DQ2 chemosensors was performed by sealing the DQ2 chemosensors with different amounts of fresh, raw salmon (sashimi) at RT (FIG. 24). After 24 hours, the DQ2 chemosensor, sealed with three pieces of raw salmon, although not demonstrating a visible absorption change, began to show some activation emission. After 48 hours, all DQ2 chemosensors showed visible absorption changes and activation emissions. This demonstrates the enhanced sensitivity of fluorescence versus absorption change for detecting biogenic amines. Samples with larger quantities of salmon produced more amine species after 24 hours, resulting in the observed visible emission. The observed absorption-based color change indicates that there are significant amounts of amine species/food fermentation present in these samples.

Further testing of the DQ2 chemosensors was performed by attaching the DQ2 chemosensors to plastic wrap, which was then used to reseal packages of yellowfin seabream (FIG. 25) and whiteleg shrimp (FIG. 26) kept at RT. After 18 hours, a visible absorption change and fluorescence activation was observed for both samples.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. An aggregation induced emission (AIE) chemosensor comprising a protonated form of a compound selected from the group consisting of:

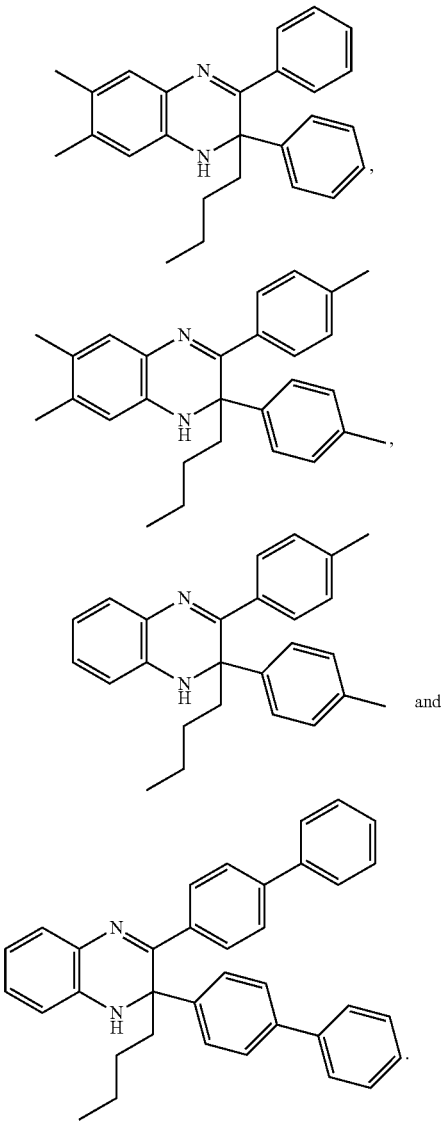

2. The AIE chemosensor of claim 1, wherein the compound is:

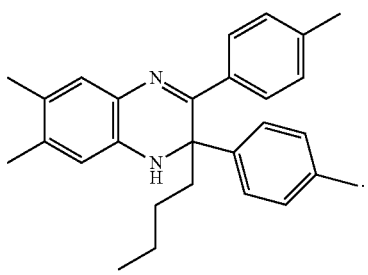

3. The AIE chemosensor of claim 1, wherein deprotonation of the protonated form of the compound produces a detectable change in light absorption.

4. The AIE chemosensor of claim 1, wherein deprotonation of the protonated form of the compound produces a detectable change in light emission.

5. The AIE chemosensor of claim 1, wherein the chemosensor exhibits aggregation induced emission upon exposure to an amine.

6. The AIE chemosensor of claim 5, wherein the amine is a gaseous amine.

7. A method of detecting food spoilage in a sample, comprising:
administering the AIE chemosensor of claim 1 to the sample; and
detecting the presence of food spoilage by measuring light emission.

8. The method of claim 7, furthering comprising waiting for a period of time after administering the AIE chemosensor and before detecting the presence of food spoilage.

9. The method of claim 7, wherein the AIE chemosensor is loaded onto a filter paper strip prior to administering the AIE chemosensor to the sample.

10. The method of claim 7, wherein the light emission is a luminescent color change from yellow to red.

11. The method of claim 7, wherein the light emission is fluorescence in response to UV excitation.

12. The method of claim 7, wherein the food spoilage is quantified by observing emission intensity.

13. The method of claim 7, further comprising determining food safety by observing emission intensity.

14. A kit for monitoring food safety, comprising:
an AIE chemosensor of claim 1;
a filter paper strip; and
a packaged food product.

15. The kit for monitoring food safety of claim 14, wherein the AIE chemosensor is loaded onto the filter paper strip.

* * * * *